(12) United States Patent
Baek

(10) Patent No.: US 11,162,885 B2
(45) Date of Patent: Nov. 2, 2021

(54) VISCOMETER AND METHODS FOR USING THE SAME

(71) Applicant: Rheosense, Inc., San Ramon, CA (US)

(72) Inventor: Seong-Gi Baek, Pleasanton, CA (US)

(73) Assignee: Rheosense, Inc., San Ramon, CA (US)

( * ) Notice: Subject to any disclaimer, the term of this patent is extended or adjusted under 35 U.S.C. 154(b) by 162 days.

(21) Appl. No.: 16/532,241

(22) Filed: Aug. 5, 2019

(65) Prior Publication Data

US 2020/0033241 A1 Jan. 30, 2020

Related U.S. Application Data

(63) Continuation of application No. 15/290,936, filed on Oct. 11, 2016, now Pat. No. 10,436,694, which is a
(Continued)

(51) Int. Cl.
*G01N 11/02* (2006.01)
*G01N 11/08* (2006.01)
(Continued)

(52) U.S. Cl.
CPC ............. *G01N 11/02* (2013.01); *G01N 11/08* (2013.01); *G01N 25/04* (2013.01); *G01N 33/487* (2013.01);
(Continued)

(58) Field of Classification Search
CPC ........ G01N 11/02; G01N 11/08; G01N 25/04; G01N 33/487; G01N 2011/002; G01N 2011/0026
See application file for complete search history.

(56) References Cited

U.S. PATENT DOCUMENTS

| 3,143,393 A | 8/1964 | De Sequin Des |
| 3,266,299 A | 8/1966 | Swank |

(Continued)

FOREIGN PATENT DOCUMENTS

| CN | 1449491 A | 10/2003 |
| CN | 101124467 A | 2/2008 |

(Continued)

OTHER PUBLICATIONS

Baek, Notice of Allowance, U.S. Appl. No. 15/290,936, dated May 14, 2019, 9 pgs.
(Continued)

*Primary Examiner* — David Z Huang
(74) *Attorney, Agent, or Firm* — Morgan, Lewis & Bockius LLP

(57) ABSTRACT

A viscometer includes a viscosity sensor with a liquid flow channel and at least two pressure sensors positioned along the liquid flow channel and configured to measure a pressure drop of a liquid flowing through the liquid flow channel, and a dispensing mechanism configured to cause dispensing of a liquid from the syringe to the viscosity sensor at a known flow rate. The dispensing mechanism and the viscosity sensor are configured to couple with a syringe configured to contain a liquid. The viscometer further includes an electronic controller configured to control operations of the dispensing mechanism and receive and process data from the viscosity sensor. The viscometer includes a sample loading interface, included in the syringe, through which the viscometer is configured to receive the liquid. The sample loading interface includes a selection valve coupled with, and located between, the viscosity sensor and the syringe.

14 Claims, 15 Drawing Sheets

Related U.S. Application Data continuation-in-part of application No. PCT/US2015/025417, filed on Apr. 10, 2015.

(60) Provisional application No. 61/978,735, filed on Apr. 11, 2014.

(51) Int. Cl.
  *G01N 25/04* (2006.01)
  *G01N 33/487* (2006.01)
  *G01N 11/00* (2006.01)

(52) U.S. Cl.
  CPC .................. *G01N 2011/002* (2013.01); *G01N 2011/0026* (2013.01)

(56) References Cited

U.S. PATENT DOCUMENTS

| | | |
|---|---|---|
| 3,683,678 A | 8/1972 | Yau |
| 3,990,295 A | 11/1976 | Renovanz et al. |
| 4,122,708 A | 10/1978 | Maier |
| 4,141,252 A | 2/1979 | Lodge |
| 4,241,602 A | 12/1980 | Han et al. |
| 4,422,210 A | 12/1983 | Bergsand et al. |
| 4,574,622 A | 3/1986 | Hatfield |
| 4,624,132 A | 11/1986 | Parnaby et al. |
| 4,793,174 A * | 12/1988 | Yau ........................ G01N 11/08 73/54.04 |
| 4,874,500 A | 10/1989 | Madou et al. |
| 4,878,378 A | 11/1989 | Harada |
| 4,894,698 A | 1/1990 | Hijikigawa et al. |
| 4,916,678 A | 4/1990 | Johnson et al. |
| 4,920,787 A | 5/1990 | Dual et al. |
| 5,029,479 A | 7/1991 | Bryan |
| 5,058,435 A | 10/1991 | Terry et al. |
| 5,165,292 A | 11/1992 | Prohaska |
| 5,189,777 A | 3/1993 | Guckel et al. |
| 5,202,939 A | 4/1993 | Belleville et al. |
| 5,225,959 A | 7/1993 | Stearns |
| 5,304,487 A | 4/1994 | Wilding et al. |
| 5,317,870 A | 6/1994 | Inagawa |
| 5,317,908 A | 6/1994 | Fitzgerald et al. |
| 5,347,851 A | 9/1994 | Grudzien, Jr. et al. |
| 5,392,117 A | 2/1995 | Belleville et al. |
| 5,485,753 A | 1/1996 | Burns et al. |
| 5,486,335 A | 1/1996 | Wilding et al. |
| 5,503,003 A | 4/1996 | Brookfield |
| 5,602,339 A | 2/1997 | Wareham |
| 5,663,503 A | 9/1997 | Dam et al. |
| 5,756,883 A | 5/1998 | Forbes |
| 5,770,160 A | 6/1998 | Smith et al. |
| 5,983,727 A | 11/1999 | Wellman et al. |
| 6,010,461 A | 1/2000 | Haniff et al. |
| 6,032,689 A | 3/2000 | Tsai et al. |
| 6,062,088 A | 5/2000 | Ingrisch et al. |
| 6,078,706 A | 6/2000 | Nau et al. |
| 6,085,596 A | 7/2000 | Jensen et al. |
| 6,203,759 B1 * | 3/2001 | Pelc ........................ B01L 3/0265 222/333 |
| 6,237,398 B1 | 5/2001 | Porat et al. |
| 6,240,770 B1 | 6/2001 | Raffer |
| 6,338,284 B1 | 1/2002 | Najafi et al. |
| 6,370,942 B1 | 4/2002 | Dunfee |
| 6,393,898 B1 | 5/2002 | Hajduk et al. |
| 6,499,336 B1 | 12/2002 | Raffer |
| 6,575,019 B1 | 6/2003 | Larson |
| 6,681,616 B2 | 1/2004 | Spaid et al. |
| 6,725,725 B1 | 4/2004 | Werner et al. |
| 6,840,092 B2 | 1/2005 | Eggen et al. |
| 6,892,583 B2 | 5/2005 | Baek |
| 7,290,441 B2 | 11/2007 | Baek |
| 7,730,769 B1 | 6/2010 | Kwon et al. |
| 2002/0011095 A1 | 1/2002 | Park et al. |
| 2002/0148282 A1 | 10/2002 | Hajduk et al. |
| 2003/0079547 A1 | 5/2003 | Baek |
| 2003/0182991 A1 | 10/2003 | Spaid et al. |
| 2004/0037739 A1 | 2/2004 | McNeely et al. |
| 2004/0123649 A1 | 7/2004 | Spaid et al. |
| 2005/0005684 A1 | 1/2005 | Chien |
| 2005/0183496 A1 | 8/2005 | Baek |
| 2005/0210964 A1 | 9/2005 | Baek |
| 2006/0003439 A1 | 1/2006 | Ismagilov et al. |
| 2006/0019407 A1 | 1/2006 | Fulton et al. |
| 2006/0162438 A1 | 7/2006 | Schofield et al. |
| 2006/0263263 A1 | 11/2006 | Shimizu |
| 2008/0125700 A1 | 5/2008 | Moberg et al. |
| 2008/0127717 A1 | 6/2008 | Lesieur |
| 2008/0134765 A1 | 6/2008 | Baek |
| 2009/0004063 A1 | 1/2009 | Higashihara et al. |
| 2009/0216465 A1 | 8/2009 | Millet |
| 2010/0071442 A1 | 3/2010 | Moon, Jr. et al. |
| 2012/0075949 A1 | 3/2012 | Norcross, Jr. |
| 2012/0096929 A1 * | 4/2012 | Baek ..................... G01N 11/08 73/54.14 |
| 2015/0168284 A1 | 6/2015 | Minton et al. |

FOREIGN PATENT DOCUMENTS

| | | |
|---|---|---|
| DE | 19750131 A1 | 6/1999 |
| DE | 10215946 A1 | 11/2003 |
| EP | 1391734 A2 | 2/2004 |
| JP | 56-157839 | 12/1981 |
| JP | 57-045430 | 3/1982 |
| JP | 58-088637 | 5/1983 |
| JP | 61-107251 | 5/1986 |
| JP | S61-190853 | 11/1986 |
| JP | 62-194441 | 8/1987 |
| JP | 6-201420 A | 7/1994 |
| JP | 07-502122 | 3/1995 |
| JP | 11-194084 | 7/1999 |
| JP | 11-248715 | 9/1999 |
| JP | 2006-322850 | 11/2006 |
| JP | 2007-528501 | 10/2007 |
| WO | WO 93/12410 A1 | 6/1993 |
| WO | WO 99/26048 | 5/1999 |
| WO | WO 2003/038388 A1 | 5/2003 |
| WO | WO 2005/086883 A1 | 9/2005 |
| WO | WO 2009/104065 A1 | 8/2009 |
| WO | WO 2015/157698 A1 | 10/2015 |

OTHER PUBLICATIONS

Baek, Notice of Allowance, U.S. Appl. No. 10/286,602, dated Sep. 29, 2004, 7 pgs.

Baek, Final Office Action, U.S. Appl. No. 11/132,093, dated Jan. 24, 2006, 10 pgs.

Baek, Office Action, U.S. Appl. No. 11/132,093, dated Aug. 8. 2005, 9 pgs.

Baek, Office Action, U.S. Appl. No. 11/078,015, dated Sep. 13, 2006, 8 pgs.

Baek, Final Office Action, U.S. Appl. No. 11/078,015, dated Mar. 27, 2007, 6 pgs.

Baek, Notice of Allowance, U.S. Appl. No. 11/078,015, dated Jul. 6, 2007, 4 pgs.

Baek, Notice of Allowance, U.S. Appl. No. 11/983,210, dated Apr. 12, 2010, 6 pgs.

Baek, Final Office Action, U.S. Appl. No. 11/983,210, dated Aug. 20, 2009, 9 pgs.

Baek, Office Action, U.S. Appl. No. 11/983,210, dated Dec. 16, 2008, 9 pgs.

Baek, Notice of Allowance, U.S. Appl. No. 13/094,710, dated Apr. 16, 2015, 7 pgs.

Baek, Final Office Action, U.S. Appl. No. 13/094,710, dated Dec. 29, 2014, 19 pgs.

Baek, Office Action, U.S. Appl. No. 13/094,710, dated Apr. 11, 2014, 17 pgs.

Baek, Office Action, U.S. Appl. No. 13/094,710, dated Dec. 24, 2015, 15 pgs.

Baek, Office Action, U.S. Appl. No. 13/094,710, dated Jul. 28, 2016, 17 pgs.

(56) References Cited

OTHER PUBLICATIONS

Baek, Office Action, U.S. Appl. No. 13/094,710, dated May 3, 2017, 17 pgs.
Baek, Final Office Action, U.S. Appl. No. 13/094,710, dated Dec. 8, 2017, 19 pgs.
Baek, Final Office Action, U.S. Appl. No. 13/094,710, dated Jun. 29, 2018, 22 pgs.
Baek, Final Office Action, U.S. Appl. No. 13/094,710, dated Apr. 18, 2019, 19 pgs.
Baek, Office Action, U.S. Appl. No. 15/290,936, dated Nov, 8, 2018, 20 pgs.
Baek, International Search Report and Written Opinion, PCT/US2011/034002, dated Jan. 18, 2012, 9 pgs.
Dziuban, J.A. et al., "Silicon Optical Pressure Sensor," Sensors and Actuators a (Physical), Apr. 1992, vol. A32, No. 1-3, pp. 628-631, Switzerland.
Chan M.A. et al., "A Micromachined Pressure Sensor with Fiber-Optic Interferometric Readout," Sensors and Actuators A (Physical), May 1994, vol. A43, No. 1-3, pp. 196-201, Switzerland.
Chien, R.D., et al., "Study on Rheological Behavior of Polymer Melt Flowing Through Micro-Channels Considering the Wall-Slip Effect," Journal of Micromechanics and Microengineering, 15, May 2005, pp. 1389-1396.
FISO Technologies, "Product Data Sheet, FOP-M In-Vivo Pressure Sensor," No Date Listed, 2 pgs.
FISO Technologies, "Technical Note Series, Fiber-Optic Pressure Transducer," Feb. 5, 2013, 4 pgs.
Lee, S.B. et al., "A Micromachined Interferometer for Dynamic High-Pressure Sensing (in automotive applications)," Sensors, Jun. 1996, vol. 13, No. 6, Helmers Publishing, USA, 1 pg.
Rheosense Inc., Communication Pursuant to Article 94(3) EPC, EP05728127.1, dated Jul. 12, 2013, 7 pgs.
Rheosense Inc., Communication Pursuant to Article 94(3) EPC, EP05728127.1, dated Mar. 13, 2009, 5 pgs.
Rheosense Inc., Communication Pursuant to Article 94(3) EPC, EP02802527.8, dated Nov. 6, 2013, 8 pgs.
Rheosense Inc., Communication Pursuant to Article 94(3) EPC. EP02802527.8, dated Jan. 18, 2011, 7 pgs.
Rheosense Inc., Intent to Grant, EP02802527.8, dated Jul. 5, 2017, 5 pgs.
Rheosense Inc., Communication Pursuant to Rules 161(2) and 162. EP15777447.2, dated Mar. 20, 2017, 2 pgs.
Rheosense Inc., First Office Action, CN201180031161.1, dated May 6, 2014, 29 pgs.
Rheosense Inc., Second Office Action, CN201180031161.1, dated Jan. 9, 2015, 21 pgs.
Rheosense Inc., Third Office Action, CN201180031161.1, dated Jun. 13, 2015, 5 pgs.
Rheosense Inc., 1st Office Action, CN201610164123.8, dated Dec. 26, 2017, 13 pgs.
Rheosense Inc., 2nd Office Action, CN201610164123.8, dated Nov. 15, 2018, 13 pgs.
Rheosense Inc., International Search Report and Written Opinion, PCTUS2008082669, dated Jun. 29, 2009, 7 pgps.
Rheosense Inc. (Baek), International Search Report and Written Opinion, PCTUS2005/007869, dated Sep. 21, 2006, 4 pgs.
Rheosense Inc., International Preliminary Report on Patentability, PCTUS2005/007869, dated Oct. 18, 2006, 4 pgs.

Rheosense Inc., International Search Report, PCTUS2002/35290, dated Mar. 24, 2003, 1 pg.
Rheosense Inc., International Preliminary Examination Report, PCTUS2002/35290, dated Nov. 8, 2004 3 pgs.
Rheosense Inc., International Search Report and Written Opinion, PCTUS2015/025417, Jul. 24, 2015, 20 pgs.
Rheosense Inc., International Prliminary Report on Patentability, PCTUS2015/025417, dated Oct. 12, 2016, 18 pgs.
Rheosense Inc., Notification to Grant Patent, CN200580014842.1, dated Dec. 2, 2010, 2 pgs.
Rheosense Inc., Second Office Action, CN200580014842.1, dated Jul. 12, 2010, 6 pgs.
Rheosense Inc., First Office Action, CN200580014842.1, dated Jan. 16, 2009, 13 pgs.
Rheosense Inc., Extended European Search Report, EP11777928.0, dated Oct. 18, 2017, 11 pgs.
Rheosense Inc., Communication Pursuant to Rules 70(2) and 70a(2), EP11777928.0, dated Nov. 7, 2017, 1 pg.
Rheosense Inc., Certificate of Patent, JP2007-502978, dated Sep. 16, 2011, 3 pgs.
Rheosense Inc., Notification of Reasons for Rejection, JP2007-502978, dated Nov. 9, 2010, 2 pgs.
Rheosense Inc., Certificate of Patent, JP2013-508172, dated Nov. 18, 2016, 4 pgs.
Rheosense Inc., Notification to Grant Patent, CN02826519.X, dated Dec. 28, 2007, 2 pgs.
Rheosense Inc., First Office Action, CN02826519.X, dated Oct. 21, 2005, 10 pgs.
Rheosense Inc., CN201580030961, Office Action, dated Aug. 31, 2018, 4 pgs.
Rheosense Inc., Certificate of Patent, JP2003-540610, dated Mar. 6, 2009, 2 pgs.
Rheosense Inc., Notification of Reason for Rejection, JP2003-540610, dated Jul. 29, 2008, 2 pgs.
Rheosense Inc., Certificate of Patent, JP2008-159808, dated Jul. 8, 2011, 3 pgs.
Rheosense Inc., Notification of Reason for Rejection, JP2008-159808, dated Dec. 14, 2010, 1 pg.
Rheosense Inc., Notification of Reason for Rejection, JP2017-504623, dated Dec. 26, 2017, 16 pgs.
Rheosense Inc., Notification of Reason for Rejection, JP2017-504623, dated Dec. 4, 2018, 17 pgs.
Rheosense Inc., Letters Patent, KR10-2004-7006615, dated Apr. 26, 2010, 2 pgs.
Rheosense Inc., KIPO's Notice of Preliminary Rejection, KR10-2004-7006615, dated Sep. 11, 2009, 7 pgs.
Rodd, et al., "The Inertio-Elastic Planar Entry Flow of Low Viscosity Elastic Fluids in Micro-Fabricated Geometries," Journal of Non-Newtonian Fluid Mechanics 129, Jan. 2005, pp. 1-22.
Wagner, C. et al., "Optical Pressure Sensor Based on a Mach-Zehnder Inteferometer Integrated with a Lateral a-Si: H p-i-n. Photodiode," IEEE Photonics Technology Letters, Oct. 1993, vol. 5, No. 10, pp. 1257-1259, USA.
Rheosense, Inc. International Preliminary Report on Patentability, PCT/US2017/056097, dated Apr. 16, 2019, 10 pgs.
Rheosense, Inc. International Search Report / Written Opinion, PCT/US2017/056097, dated Dec. 18, 2017, 12 pgs.
Rheosense Inc., European Search Report, EP 17861107.5, dated Apr. 23, 2020, 9 pgs.

* cited by examiner

818 Determine viscosity values of the liquid at a plurality of temperatures, the liquid including proteins of a first type. Determine a melting temperature of the proteins of the first type from viscosity values of the liquid at the plurality of temperatures.

820 Determine viscosity values of a second liquid at a plurality of temperatures, the second liquid including proteins of a second type. Determine a melting temperature of the proteins of the second type from viscosity values of the second liquid at the plurality of temperatures.

822 Control a temperature of the viscosity sensor

824 Controlling the temperature includes operating one or more temperature control devices

826 Maintain the temperature of the viscosity sensor at a first temperature and maintain the temperature of the syringe at a second temperature distinct from the first temperature

828 Control a temperature of the syringe

830 Mix, at the viscometer, the liquid with a solvent to obtain a mixed solution. A concentration of a solute in the mixed solution is distinct from a concentration of the solute in the liquid. Measure a viscosity of the mixed solution. Repeat the mixing and the measuring to obtain viscosity values of the mixed solution for a plurality of concentrations of the solute.

832 Move at least a portion of the liquid in the liquid flow channel back to the syringe

834 Prior to measuring the viscosity of the liquid, identify a flow rate that satisfies pressure criteria for the at least two pressure sensors

Figure 8B

836 Dispense a continuous stream of liquids to the viscosity sensor. The continuous stream of liquids includes two or more batches of test liquids. Any two adjacent batches of test liquids, of the two or more batches of test liquids, are separated by at least one inert liquid immiscible with the two adjacent batches of test liquids.

838 Dispense a cleaning solution through the liquid flow channel of the viscosity sensor 840 Flow gas through the liquid flow channel 842 Calibrate the viscometer using a preselected reference liquid independent of a user input 844 Measure one or more of: a pH, a density, and a conductivity of the liquid

Figure 8C

VISCOMETER AND METHODS FOR USING THE SAME

RELATED APPLICATIONS

This application is a continuation application of U.S. patent application Ser. No. 15/290,936, filed Oct. 11, 2016, which is a continuation-in-part of International Application No. PCT/US2015/025417, filed Apr. 10, 2015, which claims priority to U.S. Provisional Patent Application Ser. No. 61/978,735, filed Apr. 11, 2014, all of which are incorporated by reference herein in their entireties.

TECHNICAL FIELD

This application relates generally to viscometers, including but not limited to viscometers that measure viscosity of liquids utilizing a flow-through type viscosity sensor.

BACKGROUND

Viscosity is a measure of resistance of liquid to flow and its value depends on the rate of deformation for Non-Newtonian liquids as described in Dynamics of Polymeric Liquids, Vol. 1, 1987, authored by R. B. Bird, R. C. Armstrong, and O. Hassager. The rate of deformation is given by a shear rate in a unit of (time)-1. The viscosity measured at a known shear rate is "true" viscosity. The dependence of the true viscosity on shear rate is a viscosity curve which characterizes material and is an important factor to consider for efficient processing. However, in many cases, viscosity is measured under ill-defined test condition so that shear rate cannot be known or calculated. Under ill-defined conditions, the measured viscosity value is only "apparent". Since the true viscosity is measured at a known shear rate, the true viscosity is universal whereas the apparent viscosity is not. Instead, the apparent viscosity depends on the measuring system. For example, as a common practice, a torque of a spindle immersed in a sea of test liquid is measured while the spindle is being rotated at a constant speed. In this case the torque value only yields an apparent viscosity since the test condition is ill-defined and a shear rate is not known. At best, the apparent viscosity can be measured as a function of the rotational speed of the spindle. The rotational speed of the spindle can be in fact correlated with the shear rate only if a "constitutive equation" for the test liquid is known. However, a "constitutive equation" is not known for almost all Non-Newtonian liquids. Therefore, true viscosity cannot be measured with ill-defined test conditions for most non-Newtonian liquids.

Methods of viscosity measurement that give only apparent viscosities have been developed and used for quality controls in manufacturing and material characterization. Various on-line viscometers are designed for real time viscosity measurement. U.S. Pat. No. 5,317,908 (Fitzgerald et al.) and U.S. Pat. No. 4,878,378 (Harada) are concerned with systems that measure apparent viscosities for process controls. U.S. Pat. No. 6,393,898 (Hajduk et al.) describes a system that measures many test liquids simultaneously. These viscometers measure apparent viscosities. However, because of the non-universality of the apparent viscosity measurement, a correlation of the apparent viscosity of a specific sample measured with a specific method with the true viscosity has to be found separately when desired. Fundamental development of formulations for materials requires the true viscosity measurement. Also the designs of processing equipment and accessories, such as dies, molds, extrusion screws, etc., require the true viscosity of the materials. However, the apparent viscosity measurement has been used for a quick test as an indication since it is easier and faster to measure and often more economical. The true viscosity is more difficult to get and can be only measured with a few types of instruments: rheometers and capillary viscometers. The rheometers impose a precise and known shear rate on test samples, thereby measuring true viscosities. The rheometers are versatile and usually equipped to also measure other properties. Therefore they are usually expensive. Further, large amounts of samples are usually required for viscosity measurement with a rheometer. Also, rheometers are not well suited for on-line applications. Circular capillary viscometers can measure apparent and true viscosities depending on whether a proper compensation is taken into account. The capillary viscometer needs a pressure drop measurement along the capillary for viscosity. Since the capillary is circular in cross-section, only pressure at the entrance and exit can be measured. Because of this limitation, the capillary viscometer measures only apparent viscosity unless the entrance effect is corrected for by using two different capillaries with different length to diameter ratios. However, use of two capillaries makes the capillary viscometers bulky and/or time consuming. Capillary viscometers are described in U.S. Pat. No. 6,575,019 (Larson); U.S. Pat. No. 4,920,787 (Dual et al.); U.S. Pat. No. 4,916,678 (Johnson et al.); and U.S. Pat. No. 4,793,174 (Yau). Microfluidic viscometers are disclosed in U.S. Pat. No. 6,681,616 (Michael Spaid et al.) and Publication No. 2003/0182991 (Michael Spaid et al.). Residence time of a marker in a fluidic channel is used to measure the viscosity, which is not a true viscosity unless the test liquid is Newtonian. Only an apparent viscosity is measured for non-Newtonian liquids. The portable viscometer disclosed in U.S. Pat. No. 5,503,003 (Brookfield) utilizes a well-known torque measurement of a spindle rotating in a sea of liquid for viscosity measurement. As indicated, and as is well known, this method only measures apparent viscosity.

In summary, most viscosity measurement techniques yield apparent viscosity and require relatively large volumes of sample. Also, these instruments require cleaning of the parts in contact with liquid (container, spindle, etc.) before the measurement of the next sample. Such a cleaning is time consuming so that viscosity measurements typically take about 30 minutes from the set-up to the test. The larger sample volume requirement with current techniques also increases the cleaning time and waste. Therefore, there is no genuine portable viscometer which measures true viscosity for samples in small quantity and in a fast manner. The slit viscometer disclosed in my U.S. Pat. No. 7,290,441 makes it possible to measure the true viscosity of small samples. It requires, however, a precision liquid dispensing system and associated electronics to provide and control the flow of liquid through the viscometer. A simple precision liquid dispensing system which is portable and can be use with a variety of samples is not disclosed in the prior art.

SUMMARY

According to some embodiments, a portable viscosity measurement instrument or viscometer includes a miniature viscosity measurement sensor, a portable precision liquid dispensing system for forcing a liquid sample through the miniature viscosity measurement sensor, a controller for controlling operation of the viscometer, and a display for displaying the measured viscosity of the liquid. The sensor design is described in my U.S. Pat. Nos. 6,892,583 and 7,290,441, which are hereby incorporated by reference as if fully set forth herein. The portable system measures the true viscosity of a liquid and requires only small volume samples of the liquid for measurement. This application also describes a fast and easy way to obtain samples of liquid to be tested and to insert the samples of liquid into the viscometer for testing.

The portable precision liquid dispensing system in accordance with some embodiments includes a positive displacement pump which operates in conjunction with a positive displacement sample container, which will be referred to as a positive displacement pipette, in which the sample of the liquid for which the viscosity is to be measured is supplied. The pipette may be removable from and replaceable in the viscometer so that a sample of liquid to be tested can be drawn into the pipette when removed and separate from the viscometer and the pipette with the sample of liquid therein then inserted into the viscometer for measuring the viscosity of the sample of liquid in the pipette. The pipette includes a plunger that slides within the pipette to draw a sample into the pipette (this can be done by hand) and to force the sample from the pipette when in the viscometer. In one embodiment of the positive displacement pump, a precision motor drives a lead screw which moves a push back in contact with the pipette plunger when positioned in the viscometer. As the push back moves the plunger in the pipette, liquid is dispensed from the pipette into a flow passage of the miniature viscosity measurement sensor. Control electronics control operation of the precision motor to dispense the liquid to be tested from the pipette at a known flow rate into the flow passage of the miniature viscosity measurement sensor.

The miniature flow-through viscosity measurement sensor includes a micron scale flow channel combined with a pressure sensor array which measures the pressure drop of a fully developed flow of the liquid in the flow channel. In some embodiments, when a velocity field of a flow reaches a steady state (through a transition from an entrance of the flow channel), the flow is deemed to be fully developed. In some embodiments, a fully developed flow of the liquid has a same velocity profile along a length of the flow channel. For example, a velocity of a fully developed flow of the liquid at a center of the flow channel near a first end of the flow channel is identical to a velocity of the fully developed flow of the liquid at a center of the flow channel near a second end, opposite to the first end, of the flow channel. The pressure drop is proportional to the shear stress of the liquid flowing through the channel. The shear rate is proportional to flow rate. Viscosity of the sample liquid is calculated by dividing the shear stress by the shear rate. The resulting measurement of viscosity can be shown in a display. Microcontroller or microprocessor based electronics can form the controller electronics (also called herein an electronic controller) of the viscometer to control the motor of the pump and process the data from the pressure sensors. The processed data can be displayed and may also be stored and/or sent to remote devices.

In some embodiments, if temperature control of the sample is desired, the viscometer, the viscosity sensor, and/or the sample in the pipette may be conditioned to a set temperature with a Peltier based temperature control device or other generally accepted temperature control means.

In some embodiments, the viscometer is configured to store a history of measured viscosity values for various uses and/or may store a database of the known viscosity values of various liquids, such as liquids frequently expected to be measured. This allows a quick comparison of the known viscosity of a known liquid with the measured viscosity of a sample thought to be the known liquid. Discrepancies between the known value and the measured value can indicate that the test liquid is not the liquid it is thought to be or can indicate problems with the viscometer so that the viscometer can be checked.

In accordance with some embodiments, a viscometer includes a viscosity sensor with a liquid flow channel and at least two pressure sensors positioned along the liquid flow channel and configured to measure a pressure drop of a liquid flowing through the liquid flow channel. The viscometer also includes a dispensing mechanism configured to cause dispensing of a liquid from the syringe to the viscosity sensor at a known flow rate; and an electronic controller configured to control operations of the dispensing mechanism and receive and process data from the viscosity sensor.

In some embodiments, the dispensing mechanism is configured to couple with a syringe, and the syringe is coupled with the viscosity sensor and configured to contain a liquid.

In some embodiments, the viscometer includes a sample loading interface through which the viscometer is configured to receive the liquid. In some embodiments, the syringe includes the sample loading interface. In some embodiments, the sample loading interface includes a selection or switching valve (as used herein, the term "selection valve" is used throughout to represent wide ranges of valves) coupled with the viscosity sensor and the syringe and located between the viscosity sensor and the syringe.

In some embodiments, the viscometer includes a transporting device configured to couple with the syringe and the dispensing mechanism. The transporting device is configured to move the syringe between a first location for aspirating a test liquid into the syringe and a second location for coupling the syringe to the viscosity sensor, wherein the second location is distinct from the first location and the transporting device is configured to move the syringe between the first location and the second location independent of user intervention.

In some embodiments, the viscometer is configured to aspirate the test liquid into the syringe independent of user intervention.

In some embodiments, the viscometer includes a viscosity sensor module that includes a plurality of viscosity sensors.

In some embodiments, a plurality of liquid flow channels is defined in the viscosity sensor and at least two pressure sensors are positioned along each of two or more liquid flow channels of the plurality of liquid flow channels.

In some embodiments, the viscometer includes a temperature control device. In some embodiments, the temperature control device is coupled with the electronic controller and the electronic controller is configured to control the temperature control device. In some embodiments, the viscosity sensor is temperature controlled. In some embodiments, the syringe is temperature controlled.

In some embodiments, the electronic controller is configured to determine viscosity values of the liquid at a plurality of temperatures, the liquid including proteins of a first type; and determine a melting temperature of the proteins of the first type from viscosity values of the liquid at the plurality of temperatures.

In some embodiments, the electronic controller is configured to: determine viscosity values of a second liquid at a plurality of temperatures, the second liquid including proteins of a second type; and determine a melting temperature of the proteins of the second type from viscosity values of the second liquid at the plurality of temperatures.

In some embodiments, the viscometer includes a mixer coupled with the electronic controller and configured to mix the liquid with a solvent to obtain a mixed solution. A concentration of a solute in the mixed solution is distinct from a concentration of the solute in the liquid. The electronic controller is configured to: measure a viscosity of the mixed solution; and initiate repeated mixing and measuring to obtain viscosity values of the mixed solution for a plurality of concentrations of the solute.

In some embodiments, the viscometer includes a sample injector. The sample injector is configured to dispense a continuous stream of liquids to the viscosity sensor. The continuous stream of liquids includes two or more batches of test liquids. Any two adjacent batches of test liquids, of the two or more batches of test liquids, are separated by at least one inert liquid immiscible with the two adjacent batches of test liquids.

In some embodiments, the viscometer includes a pump configured to dispense a cleaning solution through the liquid flow channel of the viscosity sensor.

In some embodiments, the viscometer is configured to couple with a source of gas and provide the gas through the liquid flow channel.

In some embodiments, the gas is regulated dry gas.

In some embodiments, the viscometer is configured to determine an operation status of the viscosity sensor based on one or more measurements for the regulated dry gas.

In some embodiments, the viscometer is configured to self-calibrate by using a preselected reference liquid.

In some embodiments, the viscometer includes one or more of: a pH meter, a density meter, and a conductivity meter.

In some embodiments, the liquid flow channel comprises a rectangular liquid flow channel.

In some embodiments, the viscosity sensor has an inlet and an outlet, the inlet configured to couple with a syringe, and the viscometer further comprises a positive pressure source coupled with the outlet of the viscosity sensor.

In accordance with some embodiments, a method for performing a viscosity measurement includes receiving, at a viscometer comprising a viscosity sensor with a liquid flow channel, a liquid from a syringe into the liquid flow channel at a known flow rate. The viscometer further comprises a dispensing mechanism and an electronic controller. At least two pressure sensors are positioned along the liquid flow channel and configured to measure a pressure drop of the liquid flowing through the liquid flow channel. The electronic controller is configured to control operations of the dispensing mechanism and receive and process data. The dispensing mechanism is configured to couple with the syringe and cause dispensing of a liquid in the syringe to the viscosity sensor at the known flow rate. The method also includes measuring a viscosity of the liquid.

In accordance with some embodiments, a method for performing a viscosity measurement includes moving a syringe between a first location for aspirating a test liquid into the syringe and a second location for coupling the syringe with a viscosity sensor of a viscometer independent of user intervention. The second location is distinct from the first location. The method also includes coupling a syringe with the viscosity sensor. The viscosity sensor is with a liquid flow channel. The method further includes receiving, at the viscometer, a liquid from the syringe into the liquid flow channel at a known flow rate. The viscometer further comprises a dispensing mechanism and an electronic controller. At least two pressure sensors are positioned along the liquid flow channel and configured to measure a pressure drop of the liquid flowing through the liquid flow channel. The electronic controller is configured to control operations of the dispensing mechanism and receive and process data. The dispensing mechanism is configured to couple with the syringe and cause dispensing of a liquid in the syringe to the viscosity sensor at the known flow rate. The viscometer further comprises a sample loading interface through which the viscometer is configured to receive the liquid, wherein the syringe includes the sample loading interface. The method includes measuring a viscosity of the liquid.

BRIEF DESCRIPTION OF THE DRAWINGS

Additional features and advantages will be apparent from the detailed description which follows, taken in conjunction with the accompanying drawings, which together illustrate, by way of example, features of exemplary embodiments.

FIGS. 8A-8C are flow charts representing a method of measuring a viscosity of a liquid in accordance with some embodiments.

Reference will now be made to the exemplary embodiments illustrated, and specific language will be used herein to describe the same. It will nevertheless be understood that no limitation of the scope of the claims is thereby intended.

DESCRIPTION OF EXAMPLE EMBODIMENTS

Figure 1:
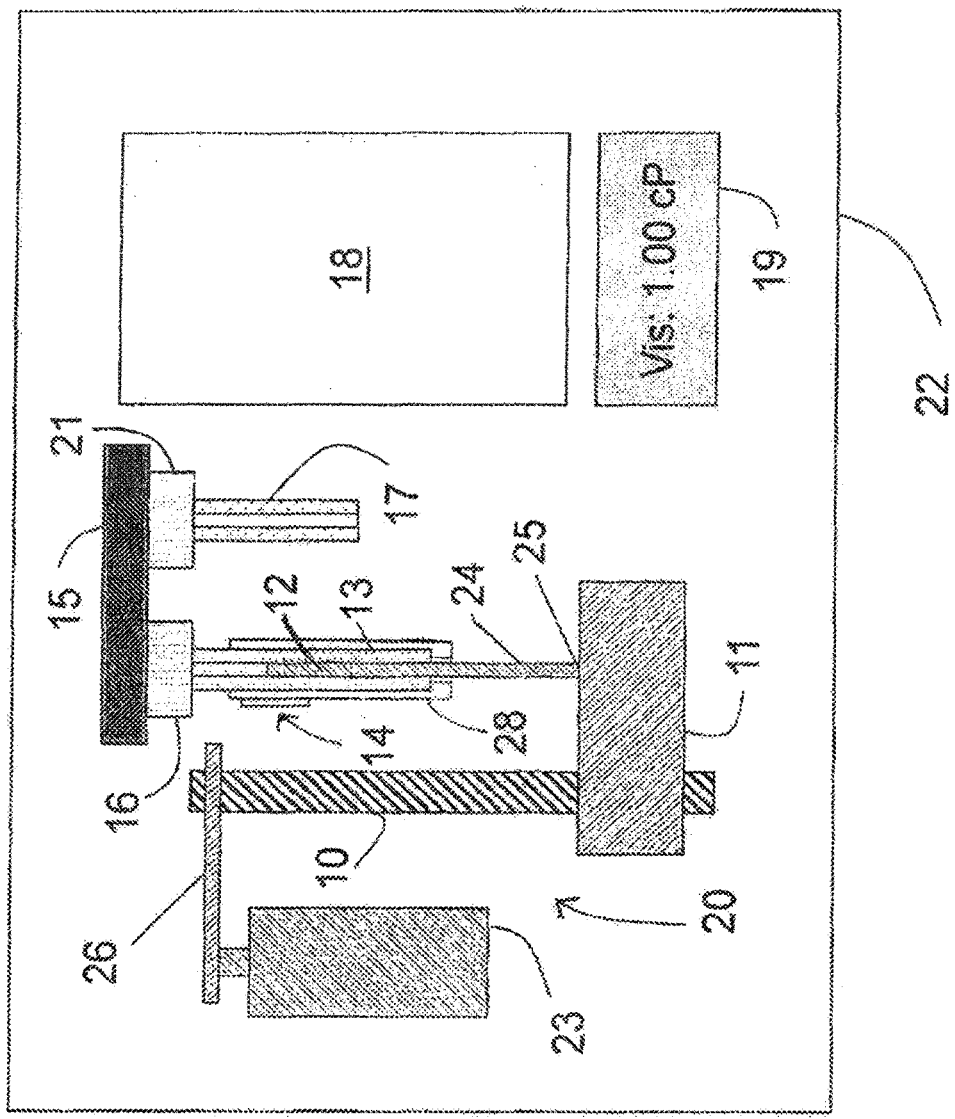
FIG. 1 is a schematic representation of a portable viscometer in accordance with some embodiments.

In accordance with some embodiments, an improved viscometer, which is portable, easier-to-use, more accurate, and a faster way of measuring the viscosities of liquid samples than prior art viscometers, is described. Referring to FIG. 1, the viscometer 22 includes a precision pump, indicated generally by reference number 20, a liquid container 14 for supplying a sample of the liquid for which a viscosity measurement is desired, a flow-through viscosity sensor 15, a controller 18, and a display 19.

The pump 20 works in conjunction with a sample container shown and referred to as a pipette 14 having a pipette barrel or body 13 and a plunger 12 slidably positioned in the pipette barrel 13 with plunger end portion 24 extending from an end of the barrel 13. The pipette 14 may be removably positioned and held in the viscometer by a mounting mechanism 28 so the pipette can be removed, filled with a sample of liquid to be tested, and replaced into the mounting mechanism of the viscometer, or can be removed and replaced with another similar pipette containing a sample of liquid to be tested. The pipette may be made disposable so a new, clean pipette is used for each sample of liquid. The pump includes a precision motor 23, a lead screw 10 rotatable by the motor 23 through a drive mechanism 26, such as a gear drive or belt drive, and a push back 11 mounted on lead screw 10 which contacts the end 25 of pipette plunger end portion 24 when pipette 14 is positioned in the viscometer. The push back 11 moves laterally along lead screw 10 in response to the rotation of the lead screw 10 by motor 23.

Figures 3, 4:
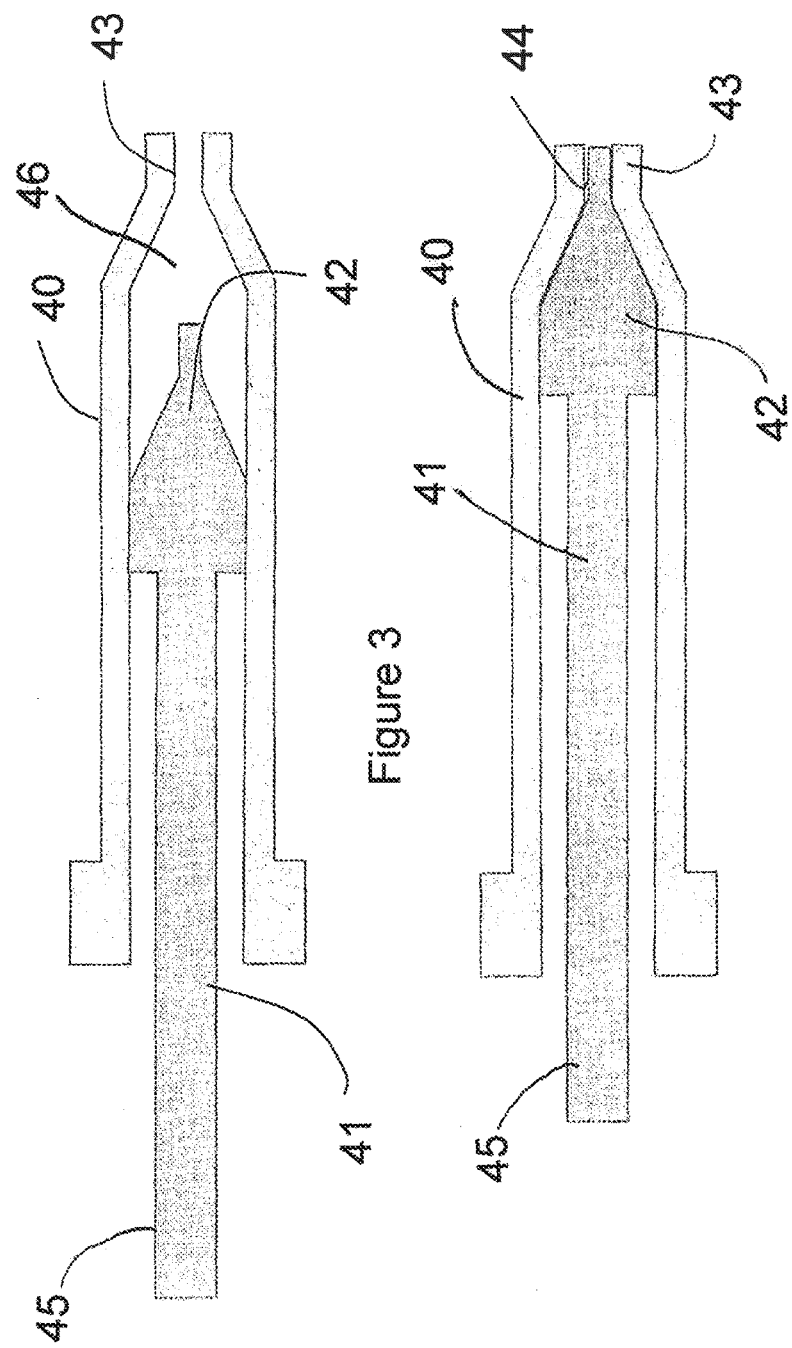
FIG. 3 is a cross-sectional view of a pipette useable in the system in accordance with some embodiments, showing the pipette plunger in an intermediate position in the pipette.
FIG. 4 is a similar cross-sectional view of the pipette of FIG. 3 in accordance with some embodiments, showing the pipette plunger in position before a sample of liquid has been drawn into the pipette or after the sample of liquid has been dispensed from the pipette.

An example of a pipette construction is shown in FIGS. 3 and 4. A pipette plunger 41 has a plunger head 42 sealingly and slidably received in pipette barrel 40 with an end portion 45 extending from an end of the pipette barrel 40. Both the pipette barrel and pipette plunger can be fabricated from plastic by injection molding. The plunger can slide back and forth inside of the barrel 40. In order to minimize air entrapment when filling the pipette with sample liquid, the end of plunger head 42 is shaped to closely fit into liquid flow barrel end 43, as shown in FIG. 4, to minimize any air gap 44 between the two. With the pipette in the condition shown in FIG. 4, the liquid flow end 43 of the pipette can be inserted into a liquid for which the viscosity is to be determined. A user can grasp the end portion 45 of the plunger 41 extending from the pipette barrel 40 and pull the plunger back from the end 43 of the pipette barrel to draw sample into the pipette barrel through an opening in barrel end 43. FIG. 3 shows the plunger 41 pulled back from the barrel end to create space 46 in the pipette barrel which will contain the liquid sample drawn into the pipette. As the pipette plunger 41 continues to be pulled back in pipette barrel 40, sample will continue to be drawn into the increasing space 46. The user stops pulling back the plunger 41 when the desired amount of sample is drawn into the pipette barrel. If the plunger 41 is pushed toward the liquid flow end 43 of the barrel 40, fluid in space 46 is discharged from the barrel 40 though the opening in barrel end 43.

Flow-through viscosity sensor 15 includes a liquid inlet connector 16 and a liquid outlet connector 21. As shown in FIG. 1, the liquid discharged from the end of the pipette barrel 13 is coupled through liquid inlet connector 16 to a liquid entrance to the viscosity sensor 15. A liquid discharge tube 17 is coupled through the liquid outlet connector 21 to guide liquid away from a liquid exit of viscosity sensor 15.

Figure 2A:
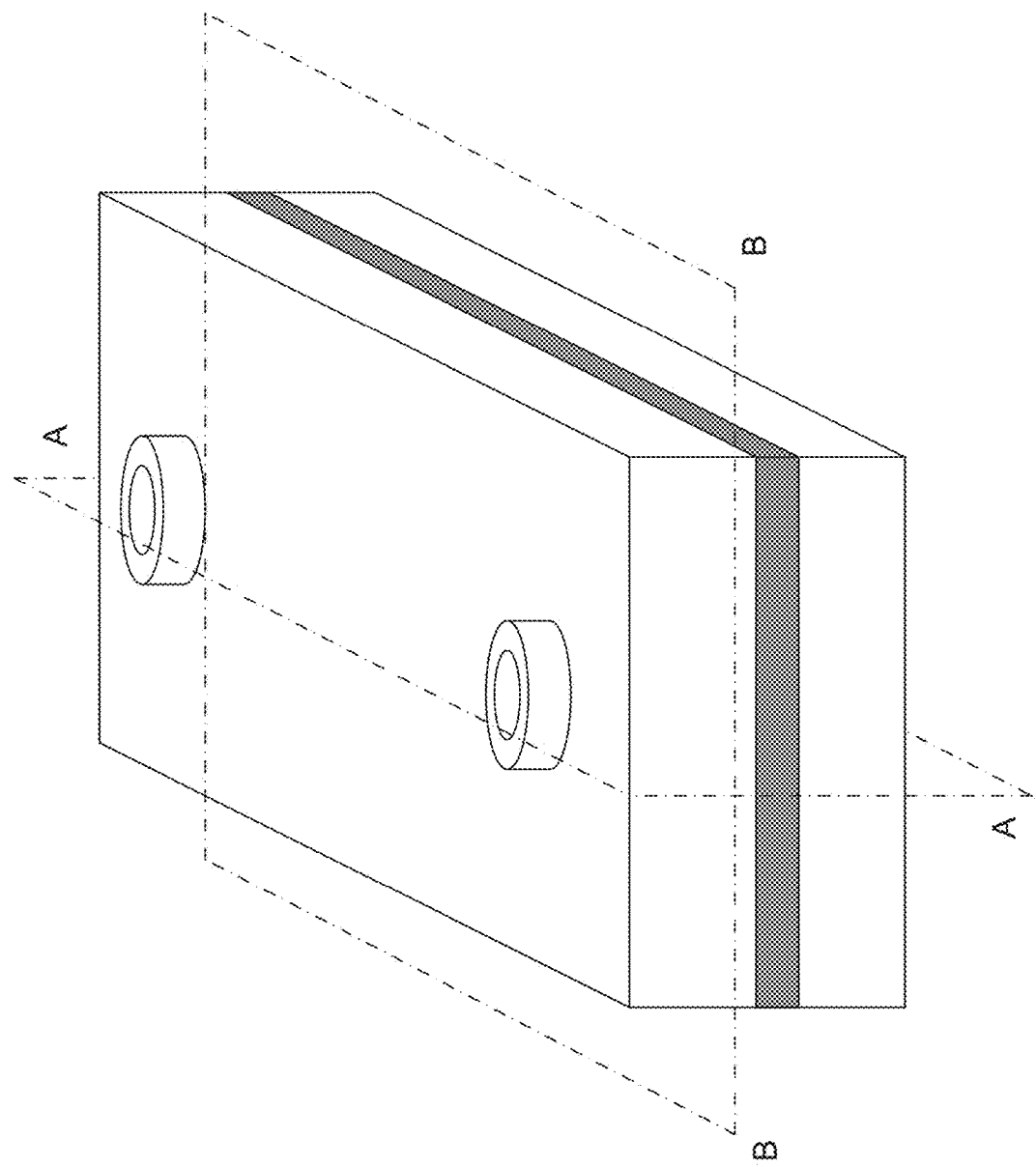
FIG. 2A is a schematic representation of a flow-through viscosity sensor in accordance with some embodiments.

FIG. 2A illustrates a perspective view of the flow-through viscosity sensor 15 in accordance with some embodiments. Also shown in FIG. 2A are planes AA and BB, which are drawn to facilitate the understanding of FIGS. 2B and 2C.

Figure 2B:
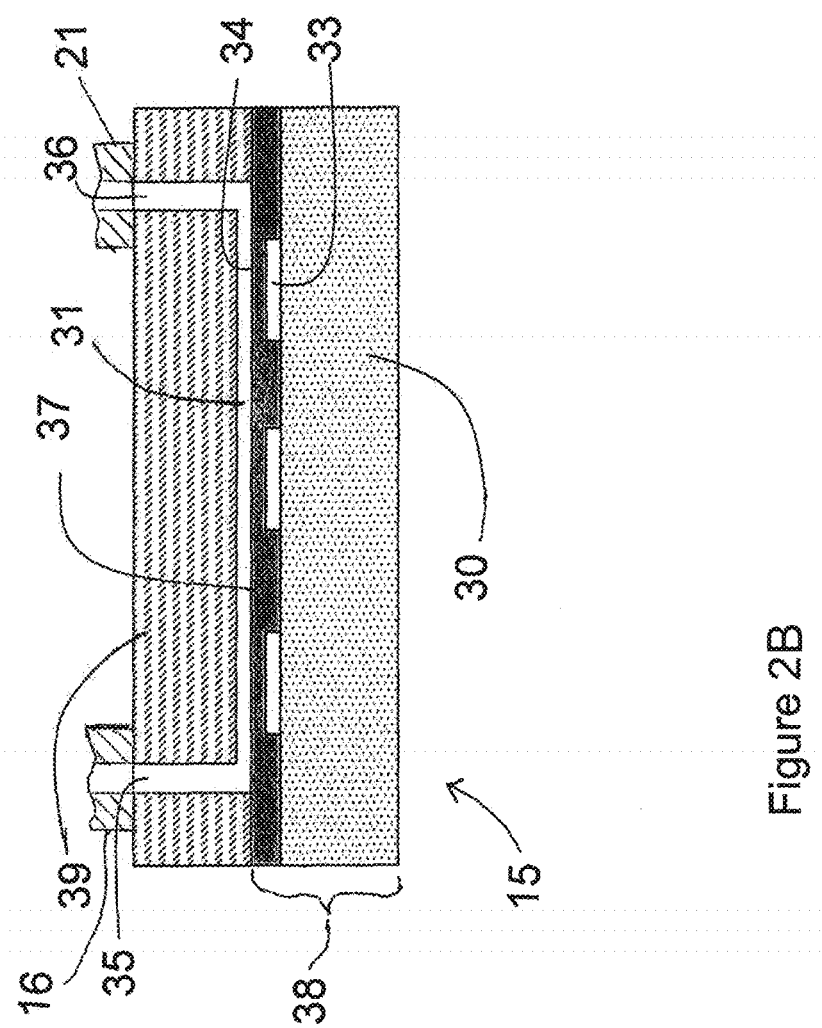
FIG. 2B is a schematic cross-sectional representation of a flow-through viscosity sensor in accordance with some embodiments.

FIG. 2B is a cross-sectional view of the flow-through viscosity sensor 15 along the plane AA (shown in FIG. 2A) in accordance with some embodiments.

Referring to FIG. 2B, the flow-through viscosity sensor 15 includes a liquid flow channel 31, with a flow channel entrance 35 and flow channel exit 36 formed in a channel substrate 39. The flow channel 31 has a rectangular cross-section with the channel substrate 39 providing three sides of flow channel 31, leaving one open side. A monolithic sensor plate 38 formed by a pressure sensor membrane 37 and a pressure sensor substrate 30 is combined with the channel substrate 39 to close the open side of flow channel 31. Monolithic sensor plate 38 provides a plurality of independent pressure sensors and is positioned with respect to the channel substrate 39 to locate at least two independent pressure sensors along the flow channel 31 spaced sufficiently away from the channel entrance 35 and channel exit 36 whereby a pressure drop of fully developed flow of liquid through the flow channel 31 can be measured by the pressure sensors. As explained above, the pressure drop is proportional to the shear stress of the liquid flowing through the channel. The shear rate is proportional to the flow rate. Viscosity of the sample liquid is calculated by dividing the shear stress by the shear rate.

In the embodiment shown in FIG. 2B, three independent pressure sensors are provided by the monolithic sensor plate 38 along flow channel 31. Each of the independent pressure sensors is formed by a cavity 33 in the pressure sensor membrane 37. The portions 34 of the pressure sensor membrane 37 that extend over the respective cavities 33 will deflect into the respective cavities 33 upon application of pressure to such portions 34 of the pressure sensor membrane extending over the respective cavities 33. The amount of deflection into a respective cavity is proportional to the pressure applied by the liquid flowing in the flow channel 31 to the pressure sensor membrane over the respective cavities.

A detector is provided in each of the cavities for detecting the displacement of the membrane into the respective cavity which provides a measurement of the pressure applied to the membrane over the cavity. Various detectors can be used, such as a capacitance detector wherein one capacitor electrode is located on the pressure sensor membrane over a cavity and the other capacitor electrode is located on the sensor substrate 30 covering the cavity. Displacement of the membrane moves the capacitor electrodes closer together and changes the capacitance which provides the measure of pressure. It will be noted that the surface of the pressure sensor membrane 37 along the liquid channel 31 is substantially a smooth continuous surface without individual pressure sensors being inserted into the surface to form irregularities and discontinuities. This smooth channel surface is important to obtaining accurate pressure measurements. A more detailed description of the pressure sensor and variations and different embodiments of the pressure sensor construction and of the flow-through viscosity sensor are provided in U.S. Pat. Nos. 6,892,583 and 7,290,441, which are incorporated by reference herein in their entireties. Liquid inlet connector 16 attached to channel substrate 39 around liquid channel entrance 35 provides for connection of a source of pressurized sample liquid, here liquid discharged from pipette 14, and liquid outlet connector 21 attached to channel substrate 39 around liquid channel exit 36 provides for connection to a sample liquid drain or holding reservoir.

Figure 2C:
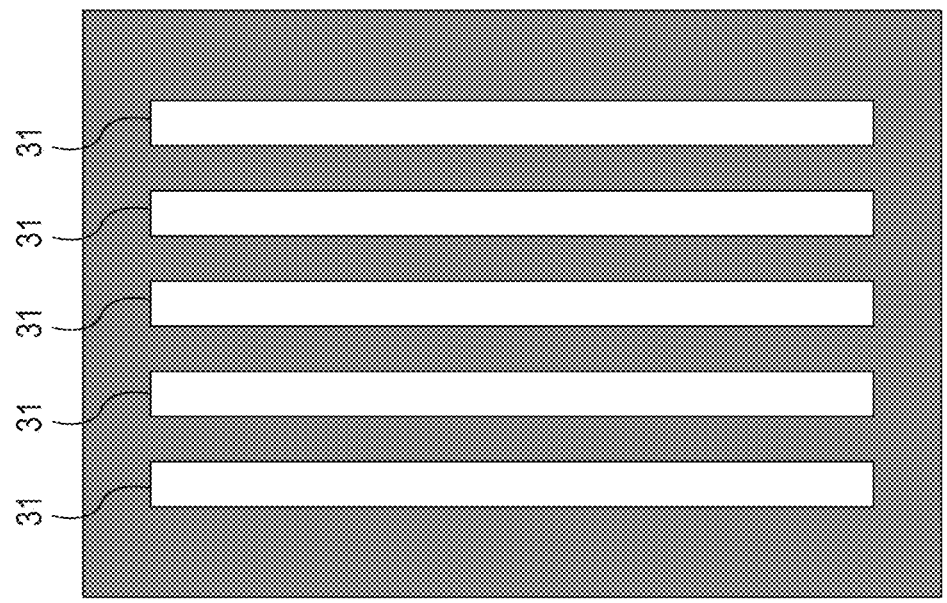
FIG. 2C is a schematic cross-sectional representation of a flow-through viscosity sensor in accordance with some embodiments.

FIG. 2C is a cross-sectional view of the flow-through viscosity sensor 15 along the plane BB (shown in FIG. 2A) in accordance with some embodiments. As illustrated in FIG. 2C, in some embodiments, a plurality of liquid flow channels is defined in the viscosity sensor. In some embodiments, at least two pressure sensors are positioned along each of two or more liquid flow channels of the plurality of liquid flow channels. In some other embodiments, only a single liquid flow channel is defined in the viscosity sensor.

In some embodiments, a plurality of viscosity sensors is formed on a single substrate, and the single substrate defines a plurality of channels for the plurality of viscosity sensors. In some embodiments, each viscosity sensor of a plurality of viscosity sensors is formed on a respective substrate.

Referring back to FIG. 1, controller 18 includes one or more microcontrollers or microprocessors, and other electrical and electronic components for controlling operation of the viscometer and peripheral components, for performing calculations, for controlling the display 19 which can display the measured viscosity and other information such as status of the viscometer, and for communicating with and transferring data to other equipment such as other computers. Communication can be through ports such as RS232 or USB ports or can be through wireless or other communication means. Controller 18 will generally include interface means, such as a keyboard, touch button pad or key pad, an external computer, or other data entry means such as buttons, a mouse, or a touch screen in display 19, whereby a user can enter control and other instruction and information into the controller.

To measure the viscosity of a sample of liquid, a sample of the liquid for which the viscosity is to be determined is obtained in a liquid sample holding pipette. The sample of liquid in the pipette can have been withdrawn from a source of the liquid into the pipette by the user of the viscometer or can be otherwise supplied to the user of the viscometer in the pipette. As shown in FIG. 1, the pipette 14 is mounted in the viscometer 22 and is held in position in the viscometer by mounting mechanism 28. The controller is then activated to control the viscometer to make a viscosity measurement. The controller will operate the motor 23 to advance the push back 11 to a position as shown in FIG. 1 against the end 25 of the pipette plunger. Alternatively, the push back 11 could be positioned, such as manually, by the user when the pipette is mounted in the viscometer prior to activation of the controller.

With the push back 11 in position against the end 25 of the pipette plunger, the controller controls the motor 23 so as to rotate lead screw 10 to advance the push back 11 and pipette plunger 12 at a desired speed or speeds to discharge the liquid from the pipette at a known desired flow rate or flow rates. As the plunger moves, the liquid is forced from the pipette into the viscosity sensor 15 and flows through the flow channel 31 in which the pressure drop of a fully developed flow of the liquid is measured by the pressure sensors of the monolithic pressure sensor 38. The pressures are measured as the local pressures over respective membrane portions of the pressure sensors along the flow channel 31 deflect sensor membrane portions 34 into respective cavities 33. The pressure drop measured along the flow channel 31 (the difference in pressures measured between successive pressure sensors along the flow channel) is proportional to the viscosity of the liquid at the specific flow rate. If the sample viscosity varies with the flow rate, then the control can be instructed to dispense the liquid at different flow rates in sequence, with or without flow stoppage. When the pressure values are acquired and the viscosity values calculated as a function of flow rate, the relationship is corrected for non-Newtonian viscosity in a known manner. The measured viscosities may be displayed on the display 19, may be stored in a controller memory or auxiliary memory, and/or transmitted to a remote memory or computer.

As the liquid is injected into liquid flow channel 31 in the viscosity sensor 15 at an initially set flow rate (or shear rate), the viscometer senses the pressure inside the liquid flow channel 31. The controller can be programmed to determine if the pressure level is optimal for the highest accuracy or assured accuracy of the viscosity measurement. If the pressure level is too low, the controller determines and sets the next flow rate value and ramps up the flow rate to the new set value. The controller continues the iteration to reach the optimal flow rate for the particular viscosity measurement. In this way, viscosity of unknown liquids can be accurately and automatically measured.

When the viscosity measurement or measurements for a sample of liquid have been obtained, the push back 11 is operated to move it back to a position to allow the used pipette to be removed and a new pipette with a sample of new liquid therein for testing to be inserted in the viscometer. The pipette with the sample of new liquid to be tested may be a new disposable pipette or a reloaded used pipette. For the new viscosity measurement, the controller operates the viscometer as described above to determine the viscosity of the sample of new liquid. In this test, the liquid from the new sample displaces the liquid from the old sample in the viscosity sensor 15. In this way, no cleaning of the viscosity sensor is needed. If the two successive liquids to be tested are not compatible or miscible, then the viscosity sensor 15 needs to be cleaned with a cleaning liquid compatible to both liquids to be tested prior to dispensing the new liquid into the viscosity sensor 15. This cleaning can be done by loading a pipette containing the cleaning liquid into the viscometer and operating the viscometer to force the cleaning liquid through the viscosity sensor 15 between the two liquids being tested.

The viscometer 22 may be powered by a battery, such as a rechargeable battery, so that it is truly portable, or may be powered by connecting it to a source of power as it is moved from place to place.

Figure 5:
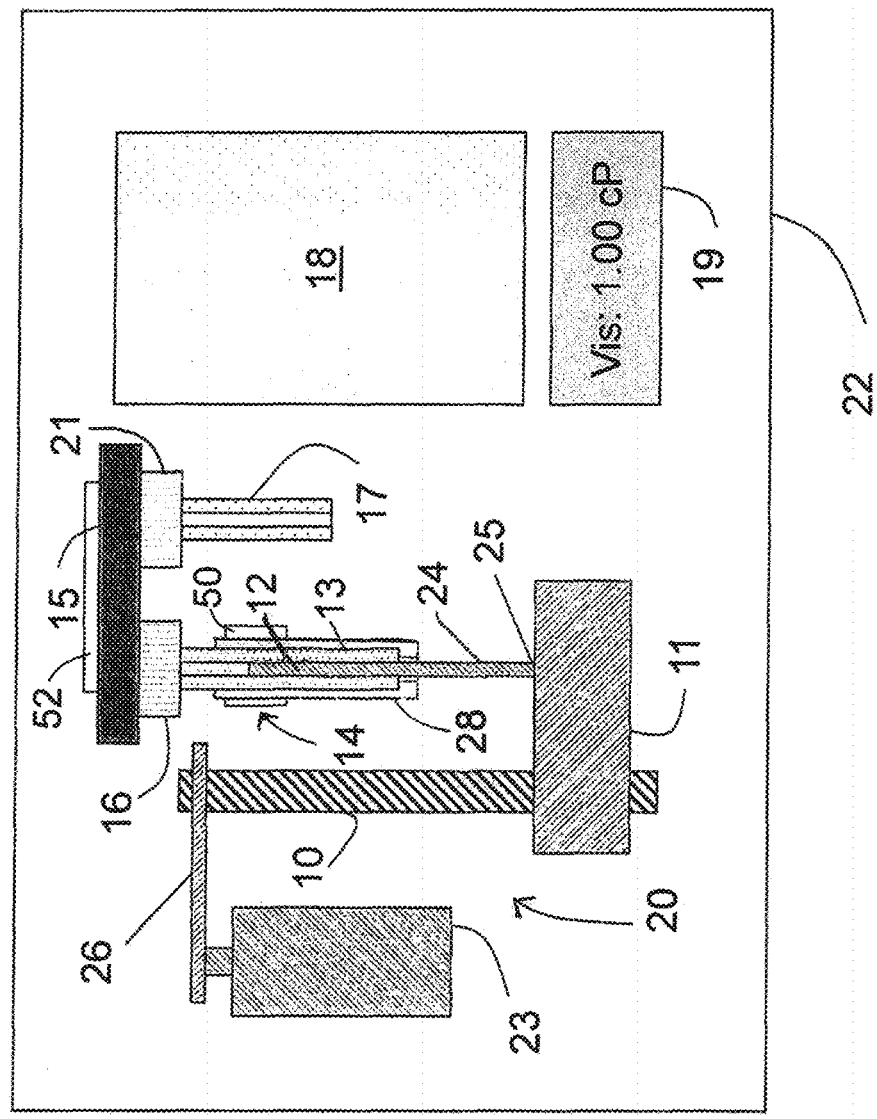
FIG. 5 is a schematic representation of a portable viscometer in accordance with some embodiments.

In some instances it may be desirable to control the temperature of the liquid for which the viscosity is being measured. If temperature control is desired, the viscometer 22, the viscosity sensor 15, and/or the sample in the pipette 14 may be conditioned at a set temperature with a Peltier based temperature control device or other generally accepted temperature control means. For example, as shown in FIG. 5, which is similar to FIG. 1, a temperature control device 50 may be placed in or in contact with pipette mounting mechanism 28 so as to heat or cool a liquid sample holding pipette 14 and the liquid sample contained therein when the pipette is mounted in the mounting mechanism 28. Depending upon how the temperature control device 50 is mounted in pipette mounting mechanism 28, the pipette mounting mechanism may also be heated or cooled to the set temperature. Some time may be required for the sample in the pipette to reach the set temperature. Similarly, a temperature control device 52 may be placed in or in contact with the viscosity sensor 15 so as to heat or cool and maintain the temperature of the material forming flow channel 31 of the viscosity sensor 15 at the set temperature. This will tend to maintain the material flowing through the flow channel 31 at substantially the set temperature. As indicated, the temperature control devices may be Peltier devices or other known temperature control devices. Further, temperature sensors can be positioned to measure the temperature of the sample liquid at various locations in the viscometer. For example, a temperature sensor can be included at one or more locations in the sensor membrane 37 along the flow channel 31 as shown in my prior referenced patents. Rather than separately controlling the temperature of separate components of the viscometer 22 as described above, the viscometer 22, or the parts thereof to be temperature controlled, may be mounted in a housing where the temperature within the housing, and thus the temperature of the entire viscometer or the parts thereof in the housing, are together temperature controlled.

As indicated in my prior referenced patents, the flow-through viscosity sensor described is very small, generally constructed of semiconductor materials or other materials used in microfabrication processes. For example, the pressure sensor membrane may be a portion of a silicon wafer, while the pressure sensor substrate and the channel substrate may be portions of a borosilicate glass wafer. The flow channel typically can be as small as about ten micrometers in width and about one micrometer in depth, with a length as short as about one hundred micrometers. Thus, the flow-through viscosity sensor is very small and small sample sizes can be used in determining viscosity. This small size of the flow-through viscosity sensor and the small amount of sample needed for viscosity testing means that the other viscometer components, such as the pipettes and the pump can also be made relatively small so the viscometer can easily be made as a relatively small portable unit.

Rather than making a portable viscometer, the same viscometer construction can be used to provide a stationary viscometer where samples of liquid to be tested can be collected from different locations in different pipettes and then transported to the viscometer and tested at the location of the viscometer.

If desired, a database of published or otherwise known viscosity values for liquids frequently measured or that might be measured can be stored in a memory in the viscometer controller. With such a database available, a user can easily display a known viscosity value from the database for a selected liquid and compare it to the viscosity value measured for a sample liquid thought to be the known liquid. Discrepancies between the published value and the measured value can indicate that the test liquid is not the liquid it is thought to be or can indicate problems with the viscometer so that the viscometer can be checked. In addition, for various reasons, it may be advantageous for a user from time to time to have access to the known viscosity values of particular liquids other than the liquid being tested at that time. Further, the viscometer may store a history of measured viscosity values with appropriate identification, again which may be used by the user of the viscometer for various purposes. For example, with such a history of measured viscosity values, a user can compare the viscosity of a liquid component being used in a manufacturing process at different times to ensure that the liquid component is within specifications required for the liquid component, or can determine and correlate a viscosity value of the component with particular desired attributes of the resulting product.

While the illustrated embodiment of the pump is shown and described in some embodiments as including a motor, lead screw, and push back to move the plunger in the pipette, various other means of moving the plunger in the pipette or of providing a precision discharge of sample liquid from a sample container can be used.

Figure 6A:
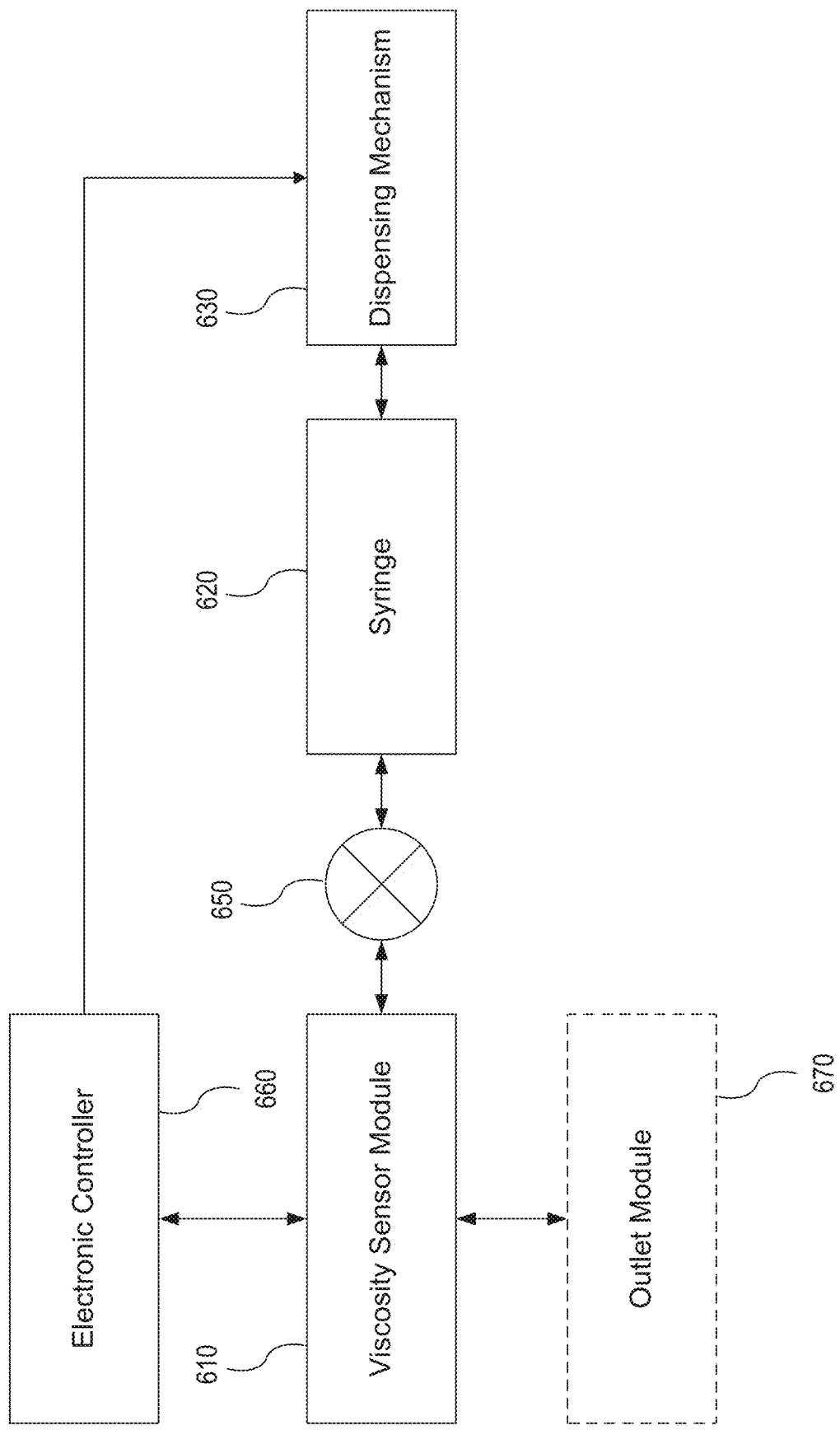
FIG. 6A is a schematic representation of a viscometer in accordance with some embodiments.

FIG. 6A is a schematic representation of a viscometer in accordance with some embodiments.

FIG. 6A illustrates that a viscometer includes a viscosity sensor module 610. In some embodiments, the viscosity sensor module 610 includes a single viscosity sensor. In some embodiments, the viscosity sensor module 610 includes a plurality of viscosity sensors. In some embodiments, a viscosity sensor has a liquid flow channel and at least two pressure sensors. The at least two pressure sensors are positioned along the liquid flow channel (e.g., a first pressure sensor located at an upstream location in the liquid flow channel and a second pressure sensor located at a downstream location in the liquid flow channel) and configured to measure a pressure drop of a liquid flowing through the liquid flow channel.

As illustrated in FIG. 6A, the viscometer also includes a dispensing mechanism 630 (e.g., the precision pump 20, FIG. 1). In some embodiments, the dispensing mechanism 630 is configured to couple with a syringe 620 (e.g., a pipette). In some embodiments, the dispensing mechanism 630 is configured to removably couple with the syringe 620. The dispensing mechanism 630 is configured to cause dispensing of a liquid from the syringe 620 to the viscosity sensor at a known flow rate. In some embodiments, the syringe 620 is coupled with the viscosity sensor. In some embodiments, the syringe 620 is removably coupled with the viscosity sensor.

FIG. 6A also illustrates that the viscometer includes an electronic controller 660 configured to control operations of the dispensing mechanism 630 and receive and process data from the viscosity sensor module 610 (or one or more viscosity sensors in the viscosity sensor module 610).

In some embodiments, the dispensing mechanism 630 comprises an autosampler. In some embodiments, the autosampler is configured to collect liquid samples from a plurality of containers (e.g., tubes, vials, or well in a plate) and sequentially dispense the collected liquid samples (e.g., dispensing a first liquid sample from a first container, followed by dispensing a second liquid sample from a second container, etc.).

In some embodiments, the viscometer includes a selection valve 650. In some embodiments, the selection valve 650 is coupled with an inlet of the viscosity sensor module 610 (or a viscosity sensor in the viscosity sensor module 610) at one end and is coupled with the syringe 620 at another end. Typically, the selection valve 650 is located between the viscosity sensor module 610 and the syringe 620. In some embodiments, the selection valve 650 is configured to receive one or more of a gas and a liquid from one or more sources other than the syringe 620. This is described below with respect to FIGS. 6C and 6E. In some embodiments, the electronic controller 660 is configured to control operations of the selection valve 650.

In some embodiments, the electronic controller 660 is configured to store predetermined viscosity values of preselected liquids (e.g., in a non-volatile memory of the electronic controller 660 or in a separate storage device that is located in the viscometer or remotely from the viscometer). In some embodiments, the predetermined viscosity values of the preselected liquids are used to identify a liquid, viscosity of which is measured by the viscometer.

In some embodiments, the viscometer also includes an outlet module 670. The outlet module 670 is coupled with an outlet of the viscosity sensor module 610 (or an outlet of a viscosity sensor in the viscosity sensor module 610). In some embodiments, the outlet module 670 is coupled with one or more outlets of viscosity sensors in the viscosity sensor module 610.

Figure 6B:
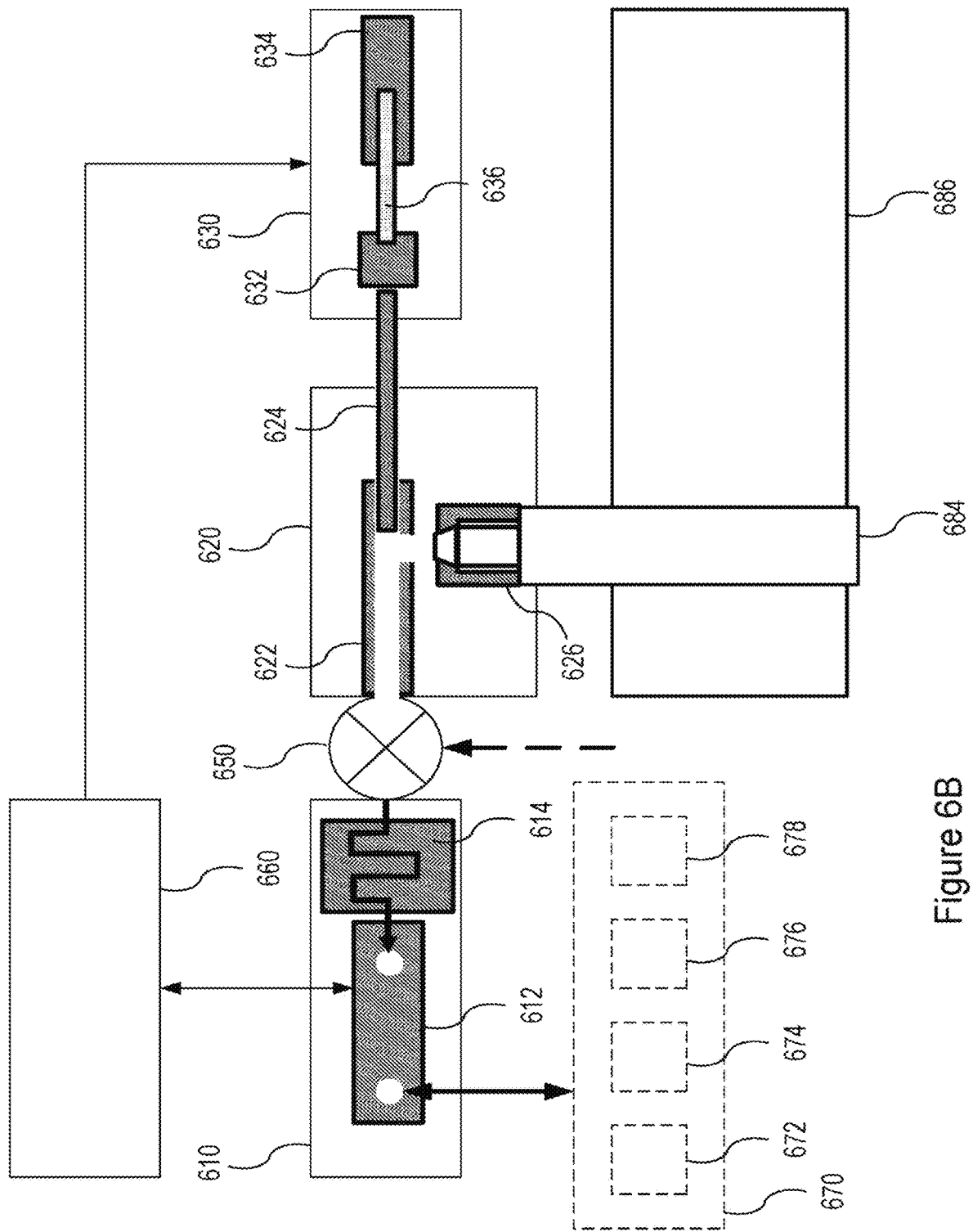
FIG. 6B is a schematic representation of a viscometer in accordance with some embodiments.

FIG. 6B is a schematic representation of a viscometer in accordance with some embodiments. The viscometer illustrated in FIG. 6B includes the viscosity sensor module 610, the dispensing mechanism 630, and the electronic controller 660, which are described above with respect to FIG. 6A. In some embodiments, certain features described above with respect to FIG. 6A are applicable to FIG. 6B. For brevity, these features are not repeated herein.

FIG. 6B illustrates that, in some embodiments, the viscosity sensor module 610 includes a viscosity sensor 612. FIG. 6B also illustrates that, in some embodiments, the viscosity sensor module 610 includes a sample preconditioner 614.

In some embodiments, the sample preconditioner 614 includes a temperature control device (e.g., a thermoelectric device, in particular, a solid-state thermoelectric device such as a Peltier device, which is configured for cooling, heating, or both). In some embodiments, the sample preconditioner 614 is configured to control a temperature of a sample liquid using the temperature control device. In some embodiments, the sample preconditioner 614 includes a temperature sensor to measure a temperature of the sample liquid.

In some embodiments, the viscosity sensor 612 in the viscosity sensor module 610 is coupled with a temperature control device. The temperature control device coupled with the viscosity sensor 612 is configured to control a temperature of the viscosity sensor 612. In some embodiments, the viscosity sensor 612 is coupled with a temperature sensor. In some embodiments, the viscosity sensor module 610 is coupled with a temperature control device. The temperature control device coupled with the viscosity sensor module 610 is configured to control a temperature of the viscosity sensor module 610. In some embodiments, the viscosity sensor module 610 is coupled with a temperature sensor. In some embodiments, the syringe 620 is coupled with a temperature control device. The temperature control device coupled with the syringe 620 is configured to control a temperature of the syringe 620. In some embodiments, the syringe 620 is coupled with a temperature sensor.

In some embodiments, the electronic controller 660 is configured to initiate operations of one or more temperature control devices (e.g., heating or cooling operations) described above. In some embodiments, the electronic controller 660 is configured to receive temperature information from one or more temperature sensors described above.

In some embodiments, the syringe 620 includes one or more of a barrel 622 and a plunger 624 (also called a piston). For example, in some embodiments, the syringe 620 includes both the barrel 622 and the plunger 624 to dispense a liquid to a viscosity sensor. In some embodiments, the syringe 620 includes a barrel 622 through which a liquid is dispensed to a viscometer, without including a plunger 624.

In some embodiments, the dispensing mechanism 630 includes one or more of an adapter 632, a motor 634, and a lead screw 636. In some embodiments, the lead screw 636 is coupled with the motor 634 and the adapter 632. For example, in some embodiments, a rotation of the motor 634 initiates a rotation of the lead screw 636, which in turn initiates a linear movement of the adapter 632 along a longitudinal direction of the lead screw 636. In some embodiments, the adapter 632 is configured to mate with the plunger 624 of the syringe 620. In some embodiments, the adapter 632 is configured to releasably mate with the plunger 624 of the syringe 620. For example, in some embodiments, a rotation of the motor 634 initiates a linear movement of the plunger 624.

FIG. 6B also illustrates that, in some embodiments, the viscometer includes a sample loading interface 626. In some embodiments, the syringe 620 is coupled with the sample loading interface 626. In some embodiments, the syringe 620 includes the sample loading interface 626. In some other embodiments, the selection valve 650 includes the sample loading interface 626. In some embodiments, the selection valve 650 is coupled with the sample loading interface 626. In some embodiments, the dispensing mechanism 630 includes the sample loading interface 626. In some embodiments, the dispensing mechanism 630 is configured to couple with the sample loading interface 626. For example, in some embodiments, the dispensing mechanism 630 includes a peristaltic pump that initiates dispensing of a liquid, received through the sample loading interface 626, to a viscometer (e.g., through the syringe 620). In such embodiments, the viscometer need not require a plunger (thus, in some embodiments, the syringe 620 does not include a plunger).

In some embodiments, the outlet module 670 includes one or more of: a positive pressure source 672, a pH meter 674, a conductivity meter 676, and a density meter 678. The pH meter 674 is configured to measure a pH of the liquid. As used herein, a pH refers to a measure of an acidity or basicity of the liquid. The density meter 678 is configured to measure a density of the liquid. The conductivity meter 676 is configured to measure a conductivity of the liquid. In some embodiments, the pH meter 674 is configured to measure a pH of the liquid concurrently with a measurement of a viscosity of the liquid (e.g., by a viscometer). In some embodiments, the density meter 678 is configured to measure a density of the liquid concurrently with a measurement of a viscosity of the liquid (e.g., by a viscometer). In some embodiments, the conductivity meter 676 is configured to measure a conductivity of the liquid concurrently with a measurement of a viscosity of the liquid (e.g., by a viscometer).

In some embodiments, the positive pressure source 672 includes a pump. In some embodiments, the pump is configured to provide a predefined pressure to an outlet of the viscosity sensor module 610 (or the viscosity sensor 612 in the viscosity module 610). In some embodiments, the positive pressure source 672 includes a pressurized gas source (e.g., a pressurized gas tank, such as a nitrogen gas tank, or a pump that provides a pressurized air). In some embodiments, a pressure provided to the outlet of the viscosity sensor module 610 by the positive pressure source 672 causes a liquid in the viscosity sensor module 610 (or the viscosity sensor 612 in the viscosity module 610) to move toward the syringe 620. In some cases, applying a negative pressure from the syringe 620 (e.g., by pulling the plunger 624) to move a liquid in the viscosity sensor 612 to the syringe 620 damages pressure sensors in the viscosity sensor 612 (e.g., in some cases, a vacuum created by the suction from the syringe 620 damages the pressure sensors in the viscosity sensor 612). Thus, applying a positive pressure to the outlet of the viscosity sensor 612 enables moving the liquid in the viscosity sensor 612 to the syringe 620 without applying a negative pressure to the viscosity sensor 612, thereby avoiding damages to the pressure sensors in the viscosity sensor 612. In some embodiments, both a positive pressure applied to the outlet of the viscosity sensor 612 and a negative pressure applied to the inlet of the viscosity sensor 612 are used to move the liquid in the viscosity sensor 612 to the syringe 620. In such embodiments, the negative pressure applied to the inlet of the viscosity sensor 612 is less than a negative pressure that is required at the inlet of the viscosity sensor 612 to move the liquid in the viscosity sensor 612 to the syringe 612 without application of a positive pressure to the outlet of the viscosity sensor 612, thereby reducing damages to the pressure sensors in the viscosity sensor 612.

In some embodiments, the provision of the pressure by the positive pressure source 672 is controlled by the electronic controller 660. For example, when the positive pressure source 672 includes a pump, the electronic controller 660 is configured to control operations (e.g., initiation and termination) of the pump. In another example, when the positive pressure source 672 includes a pressurized gas source with a control valve, the electronic controller 660 is configured to control operations (e.g., opening and closing) of the control valve. In some embodiments, the positive pressure source 672 includes a waste container.

Liquids can be provided to the viscometer in multiple ways.

In some embodiments, a liquid is first provided into a syringe before the liquid is dispensed to the viscosity module 610. In some embodiments, the barrel 622 includes a side port through which the barrel 622 is coupled with the sample loading interface 626. In some embodiments, the plunger 624 is moved to an end position, thereby allowing a sample loading through the sample loading interface 626 into the barrel 622. Then, a liquid is injected into the barrel 622. In some cases, the injected liquid fills the syringe 620 (or the barrel 622 of the syringe 620). By moving the adaptor 632 of the dispensing mechanism 630, the plunger 624 is moved to begin injection of the liquid to the viscosity sensor module 610. By controlling a speed of the adaptor 632 (and hence a speed of the plunger 624), a flow rate and a shear rate of the liquid within the viscosity sensor 612 is controlled.

In some embodiments, the injected liquid is retrieved back to the syringe 620. This is often desired if a volume of the liquid is limited or if the liquid is to be reused. In this case, the plunger 624 is pulled by a movement of the adaptor 632. In some embodiments, the positive pressure source 672 (or a positive pressure applied by the positive pressure source 672) is used to facilitate retrieving of the injected liquid. In particular, the positive pressure source 672 (or a positive pressure applied by the positive pressure source 672) greatly increases a speed of retrieving the injected liquid. Thus, in some embodiments, the injected liquid is retrieved back to the syringe 620 by a pressure applied by the positive pressure source 672. In some embodiments, the injected liquid is retrieved back to the syringe 620 primarily by a pressure applied by the positive pressure source 672. In some embodiments, the injected liquid is retrieved back to the syringe 620 solely by a pressure applied by the positive pressure source 672.

In some embodiments, an autosampler 686 (FIG. 6B) is used to provide liquids to the viscometer. The autosampler 686 is configured to receive an array of vials or wells (e.g., wells in a 96 well plate). The array of vials or wells includes respective liquids for viscosity measurements. The autosampler 686 is configured to aspirate a liquid in a vial or a well into an injector syringe 684 (which is distinct from the syringe 620 in some embodiments) and then move the injector syringe 684 to the sample loading interface 626 to load the liquid to the syringe 620. In some embodiments, the viscometer is coupled with liquid handling equipment for testing many samples unattended. In some embodiments, the liquid handling equipment is configured to retrieve a sample solution from vials in a tray or a well plate (e.g., 96-well plate or 384-well plate), In some embodiments, the syringe 620 and the dispensing mechanism 630 are integral parts of the autosampler. The autosampler is configured to position the syringe 620 for aspirating a liquid into the syringe 620, and to initiate loading the liquid into the syringe 620 using the dispensing mechanism 630. The autosampler is configured to, after the liquid is loaded into the syringe 620, move and position the syringe 620 for dispensing the liquid into an inlet of the viscosity sensor module 610, and initiate dispensing the liquid using the dispensing mechanism 630 at a controlled flow rate for a viscosity measurement. In some embodiments, all these operations are controlled by the electronic controller. In some embodiments, one or more measured viscosity values are displayed. In some embodiments, these operations are fully automated and repeated for multiple liquids, which increases a throughput of viscosity measurements.

In some embodiments, a liquid is loaded through the selection valve 650 positioned between the viscosity sensor module 610 and the syringe 620. In some embodiments, the selection valve 650 has more than two ports. For example, in some embodiments, a two-position three-port valve is used. A first port is coupled with the viscosity sensor module 610, a second port is coupled with the syringe 620, and a third port is used for receiving liquids. When the valve is in a first position, the third port and the second port are fluidically connected (e.g., a liquid provided into the third port flows into the syringe 620 through the second port) while the first port is fluidically disconnected (e.g., a liquid provided into the third port or a liquid in the syringe 620 connected to the second port does not flow into the viscosity sensor module 610). When the valve is in a second position, the first port and the second port are fluidically connected (e.g., a liquid in the syringe 620 connected to the second port flows into the viscosity sensor module 610 connected to the first port) while the third port is fluidically disconnected (e.g., a liquid provided into the third port does not flow into the viscosity sensor module 610 connected to the first port or the syringe 620 connected to the second port). While the valve is in the first position, the plunger 624 is pulled to aspirate a liquid from the third port to the syringe 620. In some embodiments, when an air gap is formed adjacent to an end of the plunger 624, additional liquid can be provided through the sample loading interfaced 626 to remove the air gap. After the liquid is loaded into the syringe 620, the valve is switched into the second position, thereby fluidically connecting the syringe 620 and the viscosity sensor module 610. Then the dispensing mechanism 630 causes dispensing of the liquid at a controlled speed or shear rate into the viscosity sensor module 610 for viscosity measurement.

In some embodiments, the syringe 620 includes a combination of injection valves. In some embodiments, the syringe 620 includes the combination of injection valves without the plunger 624 or the barrel. The combination of injection valves facilitates semi-continuous testing of liquids. In some embodiments, a liquid (also called herein a sample liquid) is provided to a sample loop of the injection valves, followed by injecting the liquid to a stream of liquids. In some embodiments, loading liquids to the sample loop and injecting the liquids to the stream of liquids are repeated. This repetition can enable semi-continuous viscosity measurements.

In some embodiments, the sample liquid is surrounded by mobile eluent. In some embodiments, the mobile eluent is miscible with the sample liquid. In some embodiments, the mobile eluent is immiscible with the sample liquid. For example, fluorocarbon is an excellent eluent. In some embodiments, the mobile eluent is provided by an immiscible liquid source 682, which is described below with respect to FIG. 6C.

In some embodiments, a liquid is loaded into the syringe 620 directly, without using the sample loading interface 626. For example, in some embodiments, the syringe 620 is decoupled from the viscosity sensor module 610 and one end of the syringe 620 (opposite to the plunger 624 of the syringe 620) is inserted into a sample liquid. The sample liquid is loaded into the syringe 620 by retracting the plunger

624. Then the syringe 620 is moved to couple with an inlet of the viscosity sensor module 610. After the syringe 620 is coupled with the inlet of the viscosity sensor module 610, the sample liquid is injected for viscosity measurement. In some embodiments, positioning and moving the positive syringe up and down are utilized using a transporting device (e.g., a robotic arm in an autosampler).

The viscometer described herein can operate in a high pressure environment (e.g., a pressure as high as 30,000 psi if the pressure sensors in the viscosity sensor 612 are configured to detect only a difference between a pressure above a sensor membrane 33 (FIG. 2B) and below the sensor membrane 33. This can be achieved by forming a vent line 31 (FIG. 2B) below the sensor membrane (33). The vent line equilibrates the pressures above (37, FIG. 2B) and below (33) the membranes under any pressure condition to which the viscosity sensor is subject. As the liquid flows through the flow channel (34, 35, 36, FIG. 2B) at a controlled flow rate, viscosity of the liquid increases the pressure above the membrane (37). The pressure increment is measured accurately by the chip (39, FIG. 2B).

In some embodiments, a liquid in the syringe 620 is maintained under a preselected pressure. In some embodiments, the dispensing mechanism 630 is maintained at a preselected pressure. This is significant, because, with a certain liquid, the viscosity of the liquid varies depending on the pressure of the liquid. With such liquid, the liquid in the syringe needs to be preserved at a desired pressure condition for accurate viscosity measurements. For example, viscosity of oil during an extraction process (e.g., from a deep well) is of great interest for petroleum operations. Oil in a deep well is typically maintained at a high pressure (e.g., an in situ pressure in a deep well, which is typically at a pressure higher than an atmospheric pressure) during an extraction process. However, measuring the viscosity of the oil at a low pressure (e.g., an atmospheric pressure) is inaccurate, because at the low pressure, volatiles in the oil, dissolved in the oil under high pressure, evaporate and change the viscosity of the oil. This process cannot be reversed simply by re-pressurizing the oil to the high pressure after volatiles in the oil have evaporated. Thus, in such application, the liquid in the syringe needs to be maintained at the preselected pressure for accurate viscosity measurements.

Figure 6C:
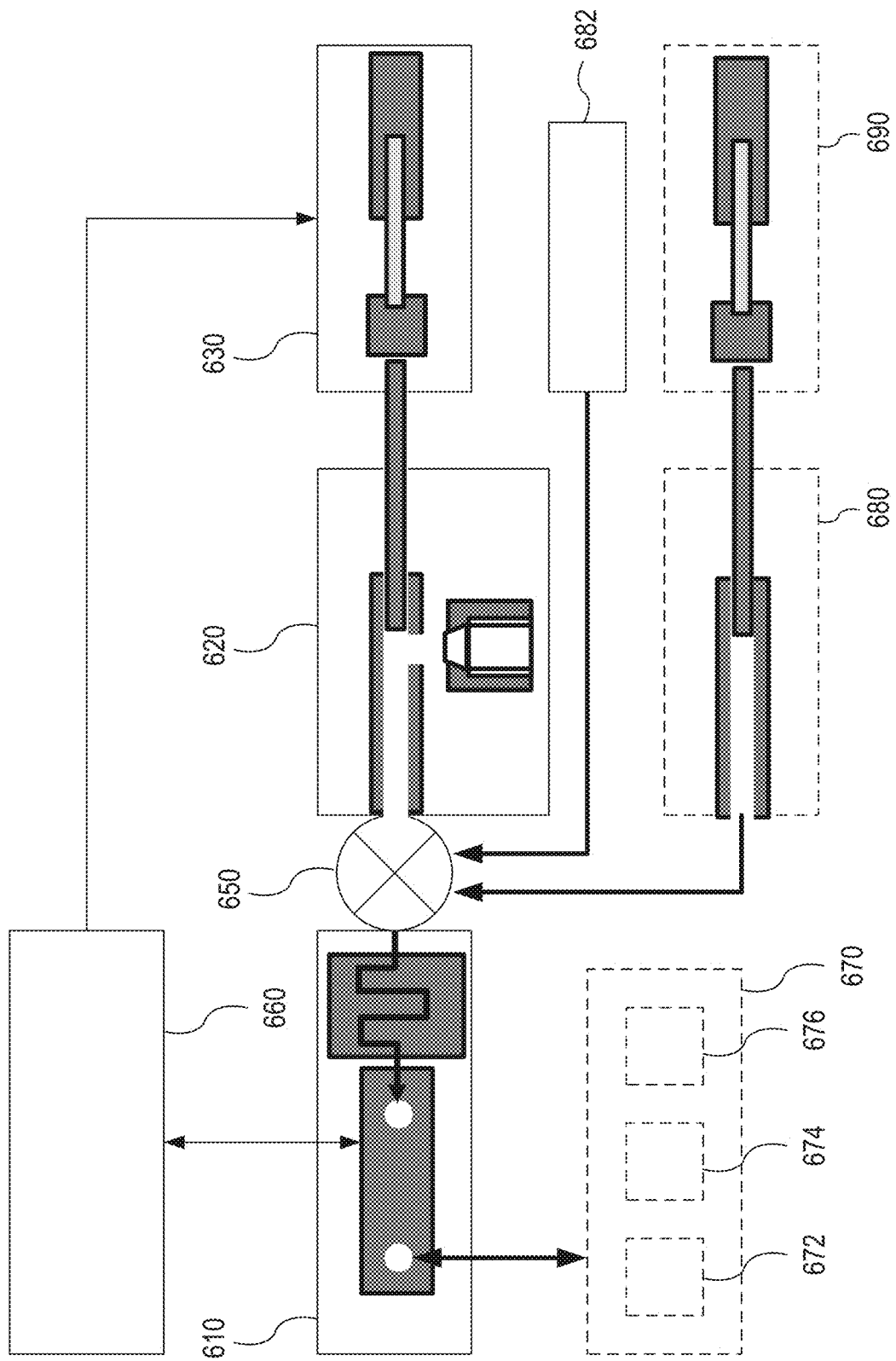
FIG. 6C is a schematic representation of a viscometer in accordance with some embodiments.

FIG. 6C is a schematic representation of a viscometer in accordance with some embodiments. The viscometer illustrated in FIG. 6C includes the viscosity sensor module 610, the dispensing mechanism 630, and the electronic controller 660, which are described above with respect to FIGS. 6A and 6B. In some embodiments, certain features described above with respect to FIGS. 6A and 6B are applicable to FIG. 6C. For brevity, these features are not repeated herein.

The viscometer in FIG. 6C also includes the selection valve 650, which is described above with respect to FIG. 6B.

In some embodiments, the selection valve 650 is coupled with a second syringe 680. In some embodiments, the viscometer includes the second syringe 680. In some embodiments, the syringe 620 is configured to provide a first liquid, and the second syringe 680 is configured to provide a second liquid. In some embodiments, the first liquid includes proteins of a first type, and the second liquid includes proteins of a second type.

In some embodiments, the second syringe 680 is coupled with a second dispensing mechanism 690. In some embodiments, the second syringe 680 is coupled with the dispensing mechanism 630 that is also coupled with the syringe 620.

In some cases, viscosity of a mixture of liquids needs to be measured. In some embodiments, the liquids are mixed first off line before the viscosity of the mixture is measured. In some embodiments, the viscometer includes a mixer configured to mix multiple liquids on line. In some embodiments, the viscometer measures a viscosity of the mixture as a function of concentration by adjusting a mixing ratio (e.g., a ratio of flow rates of the liquids). In some embodiments, the mixing ratio of the liquids is changed by changing pumping rates of one or more liquids if external pumps are used to dispense the liquids. For example, a first liquid is a solvent and a second liquid is a solution of a polymer dissolved in the solvent at a high concentration. By varying the mixing ratio, a viscosity of the mixture can be measured as a function of a polymer concentration. In some embodiments, the mixture is injected directly to an inlet of the viscosity sensor module 610. In some other embodiments, the mixture is injected first to the syringe 620. In some embodiments, the selection valve 650 is used to mix liquids. For example, in some embodiments, the selection valve 650 includes a multi-port variable-flow-rate valve configured to adjust a ratio of flow rates of multiple liquids.

In some embodiments, the selection valve 650 is coupled with an immiscible liquid source 682. In some embodiments, the immiscible liquid source 682 includes a pump and a reservoir configured to store an immiscible liquid. The immiscible liquid source 682 is configured to provide a liquid that is immiscible with liquids in the syringe 620 and the second syringe 680. For example, when the syringe 620 and the second syringe 680 include polar liquids (e.g., water), the immiscible liquid source 682 is configured to provide a non-polar liquid. In some embodiments, the electronic controller 660 is configured to control operations of the immiscible liquid source 682. In some embodiments, the electronic controller 660 is configured to initiate providing an immiscible liquid between two liquid samples entering the viscosity sensor module 610. Providing the immiscible liquid between two liquid samples prevents mixing between the two liquid samples.

Figure 6D:
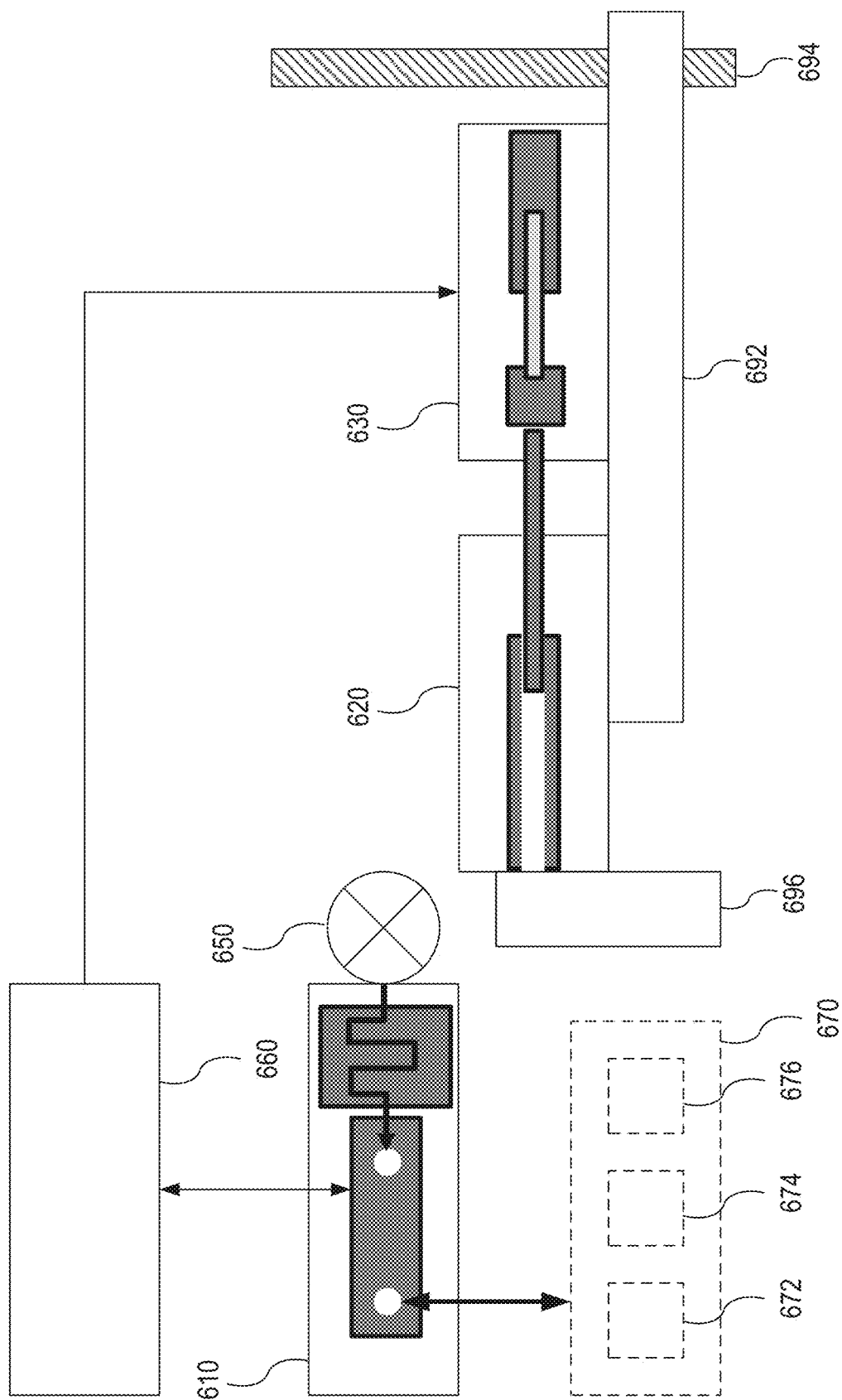
FIG. 6D is a schematic representation of a viscometer in accordance with some embodiments.

FIG. 6D is a schematic representation of a viscometer in accordance with some embodiments. The viscometer illustrated in FIG. 6D includes the viscosity sensor module 610, the dispensing mechanism 630, and the electronic controller 660, which are described above with respect to FIGS. 6A and 6B. FIG. 6D also illustrates the syringe 620, which is described above with respect to FIGS. 6A and 6B. In some embodiments, the viscometer includes the selection valve 650, which is described above with respect to FIGS. 6A-6C. In some embodiments, certain features described above with respect to FIGS. 6A-6C are applicable to FIG. 6D. For example, in some embodiments, the viscometer illustrated in FIG. 6D includes one or more of: the second syringe 680 (FIG. 6C) and the second dispensing mechanism 690 (FIG. 6C). For brevity, these features are not repeated herein.

In FIG. 6D, the viscometer also includes a transporting device 692, which is configured to couple with the syringe 620 and the dispensing mechanism 660. In some embodiments, the transporting device 692 is configured to move the syringe 620 between a first location for aspirating a test liquid into the syringe 620 (e.g., the location of the syringe 620 shown in FIG. 6D) and a second location for coupling the syringe 620 to the viscosity sensor module 610 (or a viscosity sensor in the viscosity sensor module 610) (e.g., the location of the syringe 620 shown in FIG. 6B). As illustrated in FIGS. 6B and 6D, the second location (for coupling the syringe 620 to the viscosity sensor module 610, FIG. 6B) is distinct from the first location (for aspirating a test liquid into the syringe 620, FIG. 6D). In some embodiments, the transporting device 692 is configured to move the syringe 620 between the first location and the second location independent of user intervention (e.g., without a manual input from a user). In some embodiments, the electronic controller 660 is configured to control operations of the transporting device 692.

In some embodiments, the syringe 620, when positioned at the first location, is in contact with the test liquid in a test liquid container 696 (e.g., a vial, tube, bottle, etc.). In some embodiments, the dispensing mechanism 630 is activated to initiate aspirating the test liquid into the syringe 620 (e.g., by pulling back a plunger of the syringe 620).

In some embodiments, the transporting device 692 includes a robotic arm. In some embodiments, the transporting device 692 includes one or more rotary joints. In some embodiments, the transporting device 692 includes one or more rails 694. In some embodiments, the transporting device 692 includes a belt and pulley mechanism for moving the syringe 620 between the first location and the second location. In some embodiments, the electronic controller 660 is configured to control the transporting device 692.

Figure 6E:
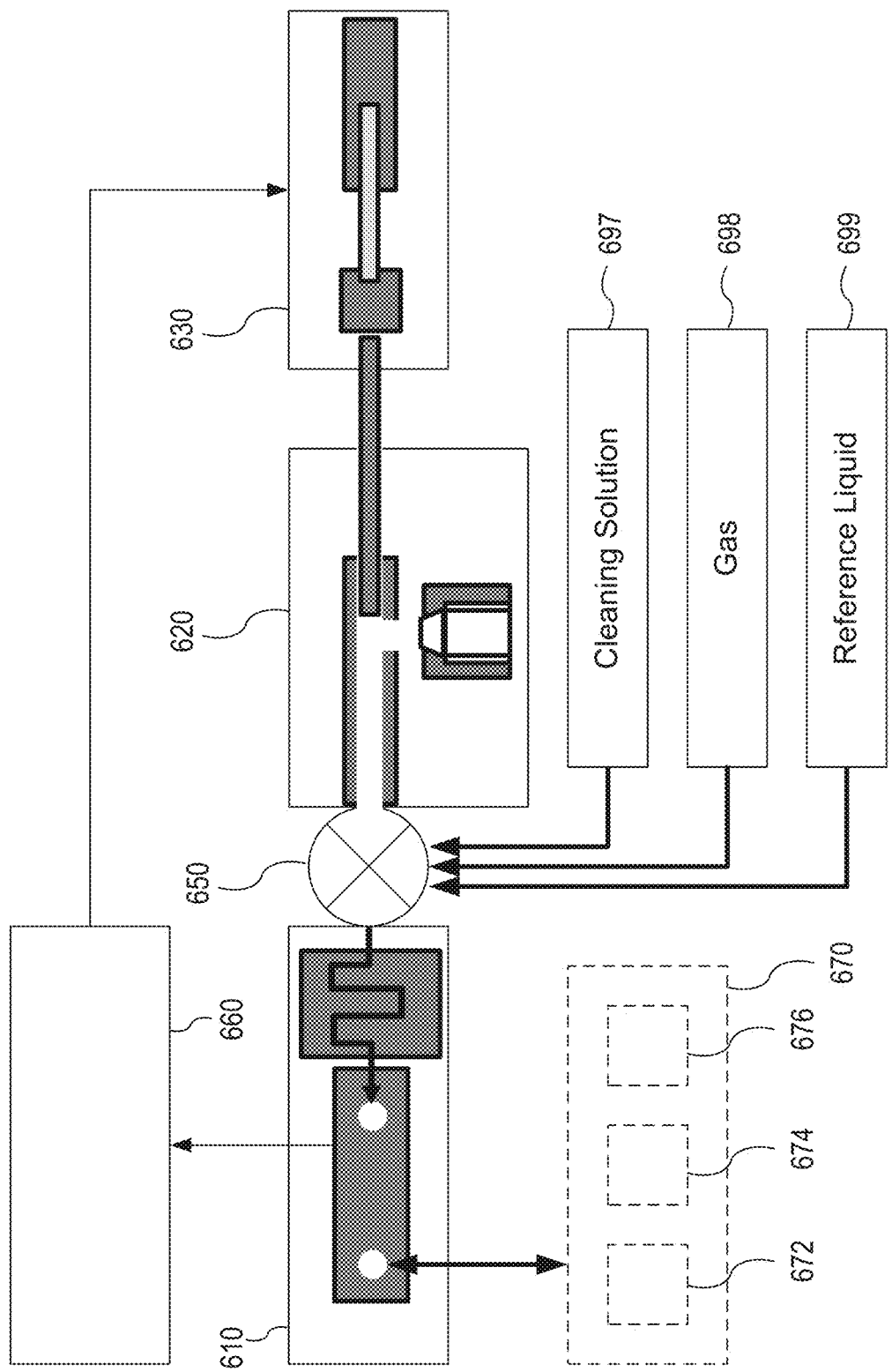
FIG. 6E is a schematic representation of a viscometer in accordance with some embodiments.

FIG. 6E is a schematic representation of a viscometer in accordance with some embodiments. The viscometer illustrated in FIG. 6E includes the viscosity sensor module 610, the dispensing mechanism 630, and the electronic controller 660, which are described above with respect to FIGS. 6A and 6B. FIG. 6D also illustrates the syringe 620, which is described above with respect to FIGS. 6A and 6B. In some embodiments, the viscometer includes the selection valve 650, which is described above with respect to FIGS. 6A-6C. In some embodiments, certain features described above with respect to FIGS. 6A-6D are applicable to FIG. 6E. For example, in some embodiments, the viscometer illustrated in FIG. 6E includes the transporting device 692 (FIG. 6D). In another example, in some embodiments, the viscometer illustrated in FIG. 6E includes the second syringe 680 (FIG. 6C) and the second dispensing mechanism 690 (FIG. 6C). For brevity, these features are not repeated herein.

In some embodiments, the selection valve 650 is coupled with one or more of: a cleaning solution source 697, a gas source 698, and a reference liquid source 699. In some embodiments, at least one of the cleaning solution source 697, the gas source 698, and the reference liquid source 699 includes a pump and a reservoir configured to store a respective gas or liquid.

In some embodiments, the cleaning solution source 697 is configured to provide a cleaning solution. For example, in some embodiments, the cleaning solution source 697 provides the cleaning solution to the selection valve 650 to clean the selection valve 650. In some embodiments, the cleaning solution source 697 provides the cleaning solution to clean the viscosity sensor module 610 (or a viscosity sensor in the viscosity sensor module 610, and in particular, a liquid flow channel of the viscosity sensor). In some embodiments, the cleaning solution source 697 provides the cleaning solution to clean the syringe 620. In some embodiments, a miscible and volatile solution is used as a cleaning solution, thereby enabling faster evaporation of the cleaning solution.

In some embodiments, the gas source 698 is configured to provide a gas. In some embodiments, the gas provided by the gas source 698 is a dry gas (e.g., dry nitrogen and clean dry air, such as −100° F. dew point air). In some embodiments, the gas source 698 provides the gas to the selection valve 650 to dry the selection valve 650. For example, any remaining liquid (e.g., a cleaning solution) is dried with the gas. In some embodiments, the gas source 698 provides the gas to dry the viscosity sensor module 610 (or a viscosity sensor in the viscosity sensor module 610). In some embodiments, the gas source 698 provides the gas to dry the syringe 620.

In some embodiments, the reference liquid source 699 is configured to provide a reference liquid. In some embodiments, the reference liquid is a liquid of a known viscosity (e.g., under one or more measuring conditions, such as at one or more temperatures). In some embodiments, the reference liquid source 699 provides the reference liquid to the viscosity sensor module 610 (or a viscosity sensor in the viscosity sensor module 610). In some embodiments, the viscosity sensor module 610 measures a viscosity of the reference liquid under one or more measuring conditions for calibration.

In some embodiments, the electronic controller 660 is configured to control operations of the cleaning solution source 697. In some embodiments, the electronic controller 660 is configured to control operations of the gas source 698. In some embodiments, the electronic controller 660 is configured to control operations of the reference liquid source 699. In some embodiments, the electronic controller 660 is configured to initiate providing a cleaning solution in response to a completion of a viscosity measurement. In some embodiments, the electronic controller 660 is configured to initiate providing a gas in response to completion of providing the cleaning solution. In some embodiments, the electronic controller 660 is configured to initiate providing a reference liquid between two liquid samples. In some embodiments, the electronic controller 660 is configured to initiate providing one or more of the cleaning solution and the gas in response to completion of providing the reference liquid.

The viscometer can be used in various applications. In some embodiments, the viscometer is used for determining a molecular size (or a molecular weight) of macromolecules. Intrinsic viscosity is related with the size of molecules. Intrinsic viscosity [η] is calculated by the equation:

$$[\eta] = \lim_{c \to 0} \left( \frac{\eta - \eta_s}{c \eta_s} \right)$$

where $\eta_s$ is a viscosity of solvent, c is a concentration of a solute (e.g., macromolecules), η is a viscosity of a solution that includes the solvent and the solute. In order to measure an intrinsic viscosity, viscosity values of solutions with different concentrations of the solute is measured. In some embodiments, by extrapolating the measured viscosity values toward a zero concentration of the solute, an intrinsic viscosity is determined.

In some embodiments, a set of solutions is prepared by mixing a macromolecular solute with a solvent at different concentrations of the macromolecular solute, and viscosity of each solution is measured. In some embodiments, the set of solutions is prepared off line (e.g., outside the viscometer). In some other embodiments, the set of solutions is prepared on-line. In some embodiments, the set of solutions is prepared using a mixer in the viscometer. For example, a first syringe is loaded with a solution at a high concentration of a solute (also called herein a stock solution) and a second syringe is loaded with a solution with a low concentration of the solute or a solution that does not include the solute (e.g., a solvent). By changing flow rates at which solutions in the first and second syringes are provided, a mixture with a different concentration of the solute is obtained. In this way, concentration can be changed continuously or in a discrete manner.

The intrinsic viscosity is related with a molecular weight of the macromolecules in accordance with the Mark-Houwink-Sakurada equation:

$$[\eta]=KM^a$$

where M is the molecular weight and K and a are parameters that depend solely on a temperature of the solution. Thus, in some embodiments, a molecular weight of a macromolecule (e.g., a protein) is determined from the intrinsic viscosity of the solution and values of K and a for the temperature of the solution using the Mark-Houwink-Sakurada equation. In some embodiments, the viscometer stores predetermined values of K and a for a plurality of temperatures.

In some embodiments, the viscometer is used for determining a melting temperature of proteins (e.g., macromolecular proteins). A melting temperature of a protein is defined to be a threshold temperature at which the protein becomes denatured. At the melting temperature, the protein typically loses its function (which is often described as a loss of its efficacy). The melting temperature of the protein is known to be related with a stability of the protein in solutions. Therefore, the melting temperature of a protein has a significant importance in biological and chemical reactions. Circular dichroism and differential scanning calorimetry have been used to measure a melting temperature of a protein. However, these traditional methods have limitations. For example, in many practical applications, protein concentrations are low, which make accurate measurements by these traditional methods challenging. In addition, a holdup time or duration during which a solution is subject to a constant temperature is an important parameter in determining a melting temperature of proteins. With traditional methods, a temperature of the protein is ramped up or down with a constant scan rate, the holdup time cannot be varied independently, thereby making accurate determination of the melting temperature challenging. Furthermore, correlating a change of viscosity of a solution with a melting temperature of a protein in the solution has remained challenging. In particular, solutions in the traditional rheometers remain exposed to air, and an evaporation of a solvent in the solution and premature denaturation of proteins led to inaccurate viscosity measurements. Other traditional methods, such as traditional methods based on circular dichroism are not capable of measuring viscosity of a solution with a high protein concentration.

In summary, traditional viscometers measure apparent viscosity, instead of intrinsic viscosity, and require a large volume of a liquid. The large liquid volume requirement with traditional viscometers also increases a cleaning time and a wasted volume of cleaning solutions. Unlike traditional viscometers, viscometers described herein are configured to measure accurately a melting temperature of proteins. In at least one aspect, a solution is fully enclosed in viscometers described herein, an evaporation of the solution (or a solvent in the solution) is none. Thus, a solute concentration is precisely preserved for a high accuracy of viscosity measurement.

Figure 7:
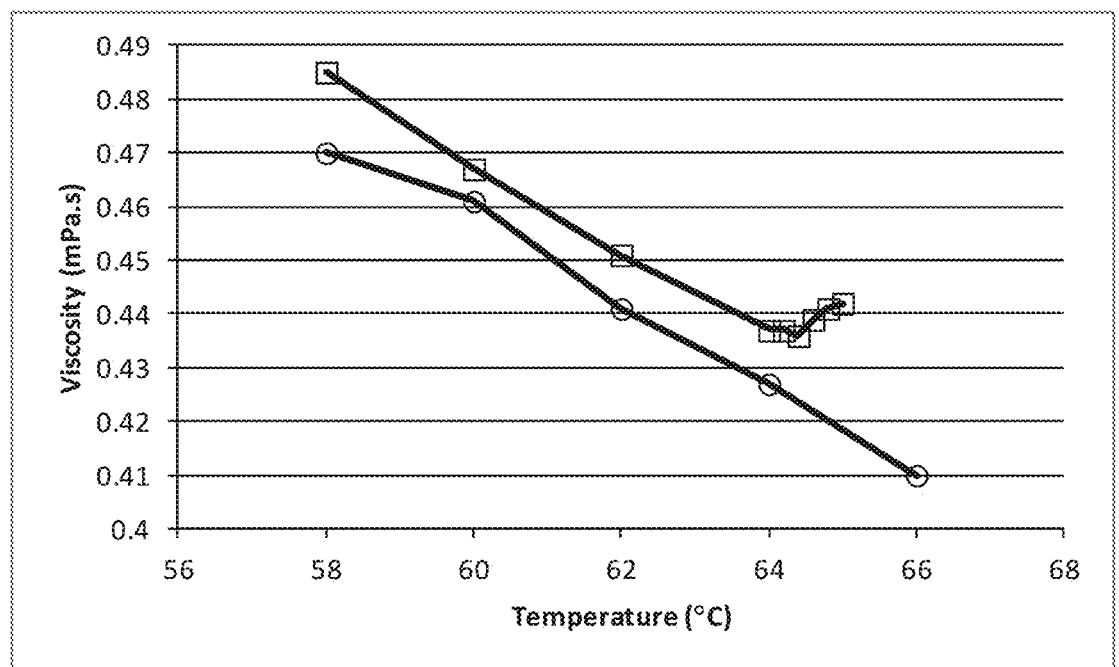
FIG. 7 is a chart that illustrates a method of determining a melting temperature in accordance with some embodiments.

In some embodiments, viscosity of a macromolecule is measured as a function of temperature. FIG. 7 is a chart that illustrates a method of determining a melting temperature in accordance with some embodiments. FIG. 7 shows viscosity of a phosphate buffered saline (PBS) for a plurality of temperatures (indicated with circular markers). As shown in FIG. 7, viscosity of the phosphate buffered saline decreases monotonically with an increasing temperature. FIG. 7 also illustrates that viscosity of a bovine gamma globulin solution (e.g., 3 mg/ml bovine gamma globulin solution) decreases with an increasing temperature for a temperature range of 62° C. and below (indicated with square markers). FIG. 7 further illustrates that viscosity of the globulin solution levels off or increases at 64° C. and above. The temperature at the point of leveling off or increase in viscosity is related to the melting temperature. Thus, in this example, a melting temperature of a globulin is determined to be 64° C.

Figure 8A:
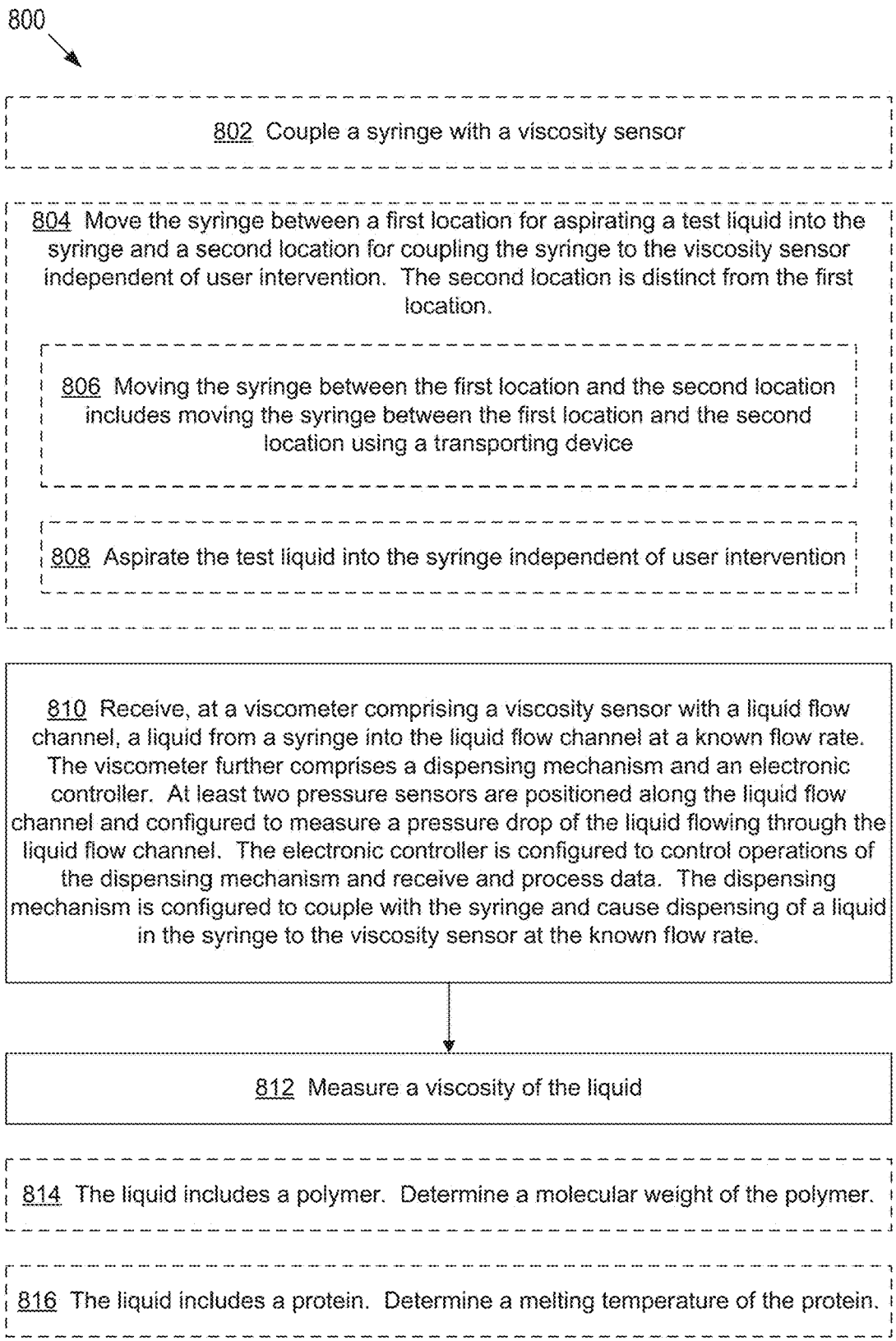

FIGS. 8A-8C are flow charts representing a method 800 of measuring a viscosity of a liquid in accordance with some embodiments.

In some embodiments, each of the following operations is performed by the viscometer, independent of user intervention (e.g., without user intervention).

In some embodiments, the method includes (802) coupling a syringe with a viscosity sensor (e.g., in FIG. 6B, the syringe 620 is coupled with the viscosity sensor 612 in the viscosity sensor module 610). In some embodiments, the syringe is communicably coupled with the viscosity sensor so that the syringe is configured to dispense a liquid to the viscosity sensor (e.g., a liquid flow channel in the viscosity sensor).

In some embodiments, the syringe includes the sample loading interface (e.g., in FIG. 6B, the syringe 620 includes the sample loading interface 626).

In some embodiments, the method includes (804) moving the syringe between a first location for aspirating a test liquid into the syringe and a second location for coupling the syringe to the viscosity sensor independent of user intervention. The second location is distinct from the first location. For example, as shown in FIGS. 6B and 6D, the syringe 620 is moved between the first location (as shown in FIG. 6D) and the second location (as shown in FIG. 6B).

In some embodiments, moving the syringe between the first location and the second location includes (806) moving the syringe between the first location and the second location using a transporting device. For example, as shown in FIG. 6D, the syringe is moved between the first location and the second location using the transporting device (e.g., a robotic arm). FIG. 6B does not illustrate the transporting device 692, but a person having ordinary skill in the art would understand that the transporting device 692 can move the syringe from the first location illustrated in FIG. 6D to the second location illustrated in FIG. 6B.

In some embodiments, the method includes (808) aspirating the test liquid into the syringe independent of user intervention. In some embodiments, as shown in FIG. 6D, the dispensing mechanism 630 is used to aspirate a test liquid into the syringe 620 by pulling a plunger of the syringe 620. In some embodiments, the test liquid is stored in a pressurized container and is forced into the syringe 620 without using the dispensing mechanism 630.

The method includes (810) receiving, at a viscometer comprising a viscosity sensor (e.g., the viscosity sensor 612, FIG. 6B) with a liquid flow channel, a liquid from a syringe into the liquid flow channel at a known flow rate. The viscometer includes a dispensing mechanism (e.g., the dispensing mechanism 630, FIG. 6B) and an electronic controller (e.g., the electronic controller 660, FIG. 6B). At least two pressure sensors are positioned along the liquid flow channel and configured to measure a pressure drop of the liquid flowing through the liquid flow channel (e.g., FIG. 2B). The electronic controller (e.g., the electronic controller 660, FIG. 6B) is configured to control operations of the dispensing mechanism and receive and process data. The dispensing mechanism is configured to couple with the syringe and cause dispensing of a liquid in the syringe to the viscosity sensor at the known flow rate.

The method includes (812) measuring a viscosity of the liquid. In some embodiments, the viscosity of the liquid is measured using the viscosity sensor module 610 (or the viscosity sensor 612 in the viscosity sensor module 610, FIG. 6B). Measurement of a viscosity of a liquid is described above with respect to FIG. 2B, and is not repeated for brevity.

In some embodiments, the viscometer includes a sample loading interface (e.g., the sample loading interface 626, FIG. 6B) through which the viscometer is configured to receive the liquid.

In some embodiments, a plurality of liquid flow channels is defined in the viscosity sensor and at least two pressure sensors are positioned along each of two or more liquid flow channels of the plurality of liquid flow channels. For example, liquid flow channels 31 shown in FIG. 2C are defined in a single viscosity sensor.

In some embodiments, the viscometer includes a viscosity sensor module that includes a plurality of viscosity sensors. For example, in some embodiments, each liquid flow channel 31 illustrated in FIG. 2C is used by a respective viscosity sensor. In some embodiments, the plurality of viscosity sensors is located in a single viscosity sensor module. In some embodiments, the multiple viscosity sensors increase a dynamic range of shear rates that can be measured by the viscometer. In some embodiments, the dynamic range of shear rates is increased by including multiple viscosity sensor modules, multiple syringes, and multiple dispensing modules. For example, a first combination of a first viscosity sensor module and a first syringe is configured to measure a first range of shear rates, and a second combination of a second viscosity sensor module and a second syringe is configured to measure a second range of shear rates that is distinct from the first range of shear rates. Combining the two ranges of shear rates allows viscosity measurements in a wider range of shear rates. This is desirable in certain applications. In some embodiments, a combination of multiple viscosity sensor modules, multiple syringes, and multiple dispensing modules is used to increase a throughput of viscosity measurements.

In some embodiments, the liquid includes (814) a polymer (e.g., a macromolecule), and the method further includes determining a molecular weight of the polymer.

In some embodiments, the liquid includes (816) a protein, and the method further includes determining a melting temperature of the protein.

In some embodiments, the method includes (818) determining viscosity values of the liquid at a plurality of temperatures, the liquid including proteins of a first type (e.g., globular proteins); and determining a melting temperature of the proteins of the first type from viscosity values of the liquid at the plurality of temperatures. In some embodiments, determining the melting temperature of the proteins of the first type includes identifying a temperature at which viscosity of the proteins of the first type increases or levels off with an increasing temperature. In some embodiments, determining the melting temperature of the proteins of the first type includes identifying an inflection point in a viscosity-temperature plot for the proteins of the first type.

In some embodiments, the method includes (820) determining viscosity values of a second liquid at a plurality of temperatures. The second liquid includes proteins of a second type (e.g., fibrous proteins). The method also includes determining a melting temperature of the proteins of the second type from viscosity values of the second liquid at the plurality of temperatures. Details of determining the melting temperature of the proteins of the first type are applicable to determining the melting temperature of the proteins of the second type, and thus, are not repeated for brevity.

In some embodiments, the method includes (822) controlling a temperature of the viscosity sensor. In some embodiments, controlling the temperature includes (824) operating one or more temperature control devices (e.g., one or more thermoelectric heating or cooling devices).

In some embodiments, the method includes (826) maintaining the temperature of the viscosity sensor at a first temperature and maintaining the temperature of the syringe at a second temperature distinct from the first temperature. In some embodiments, the method includes maintaining the temperature of the viscosity sensor and the temperature of the syringe at a same temperature.

In some embodiments, the method includes (828) controlling a temperature of the syringe. In some embodiments, controlling the temperature includes operating one or more temperature control devices (e.g., one or more thermoelectric heating or cooling devices).

In some embodiments, the method includes (830) mixing, at the viscometer, the liquid with a solvent to obtain a mixed solution. A concentration of a solute in the mixed solution is distinct from a concentration of the solute in the liquid. The method also includes measuring a viscosity of the mixed solution. The method further includes repeating the mixing and the measuring to obtain viscosity values of the mixed solution for a plurality of concentrations of the solute. In some embodiments, the method includes determining intrinsic viscosity of the liquid from viscosity values of the mixed solutions. In some embodiments, determining intrinsic viscosity of the liquid includes extrapolating viscosity values of the mixed solutions to obtain a likely viscosity value for a solution that does not include the solute.

In some embodiments, the method includes (832) moving at least a portion of the liquid in the liquid flow channel back to the syringe. This enables multiple viscosity measurements with a limited volume of a liquid. For example, in some embodiments, viscosity of the liquid is measured at a plurality of temperatures using the liquid moved back from the liquid flow channel into the syringe.

In some embodiments, the method includes (834), prior to measuring the viscosity of the liquid, identifying a flow rate that satisfies pressure criteria for the at least two pressure sensors. For example, in some embodiments, the viscometer determines whether a fully developed flow of the liquid is present in a liquid flow channel of a viscosity sensor prior to measuring the viscosity of the liquid.

In some embodiments, the method includes (836) dispensing a continuous stream of liquids to the viscosity sensor. The continuous stream of liquids includes two or more batches of test liquids. Any two adjacent batches of test liquids, of the two or more batches of test liquids, are separated by at least one inert liquid immiscible with the two adjacent batches of test liquids. The two adjacent batches are adjacent to each other in a sequence of batches in the continuous stream of liquids. However, in some embodiments, the two adjacent batches do not contact each other, because the two adjacent batches are separated by an immiscible liquid.

In some embodiments, the method includes (838) dispensing a cleaning solution through the liquid flow channel of the viscosity sensor. In some embodiments, dispensing the cleaning solution through the liquid flow channel of the viscosity sensor includes cleaning the liquid flow channel of the viscosity sensor. In some embodiments, the method includes dispensing the cleaning solution to a selection valve. In some embodiments, dispensing the cleaning solution to the selection valve includes cleaning the selection valve. In some embodiments, the method includes dispensing the cleaning solution to the syringe. In some embodiments, dispensing the cleaning solution to the syringe includes cleaning the syringe.

In some embodiments, the method includes (840) flowing gas through the liquid flow channel. In some embodiments, flowing gas through the liquid flow channel includes drying the liquid flow channel. In some embodiments, the method includes providing the gas to a selection valve. In some embodiments, providing the gas to the selection valve includes drying the selection valve. In some embodiments, the method includes providing the gas to the syringe. In some embodiments, providing the gas to the syringe includes drying the syringe. In some embodiments, the gas comprises clean dry air. In some embodiments, the gas comprises dry nitrogen gas.

In some embodiments, the method includes diagnosing the viscometer using a dry air with a preset pressure, which is used for determining a health of the viscometer. For example, in some embodiments, a pressure regulated dry air is directed to the viscometer. The viscometer then measures pressures in the chip (e.g., using the at least two pressure sensors). In some embodiments, the measured pressures are converted into a flow rate using the known viscosity of the air. By comparing the measured flow rate with a predetermined flow rate of a healthy viscometer chip (or a predetermined range of flow rates of a healthy viscometer chip), the health of the viscometer (and the path connecting the chip and the air source) is diagnosed prior to injecting samples. Checking the health of the viscometer prior to injecting a sample is useful. In particular, checking the health of the viscometer prior to injecting a sample avoids wasting a precious sample due to malfunction of the viscometer.

In some embodiments, the method includes coupling the viscometer with a source of gas. The gas is regulated dry gas. The method also includes providing the gas through the liquid flow channel; performing a measurement with the viscosity sensor; and determining whether the viscosity sensor is operating within predefined criteria based on the measurement performed with the viscosity sensor (e.g., whether the liquid flow channel is blocked and/or narrowed).

In some embodiments, performing the measurement with the viscosity sensor includes measuring pressures of the gas within the viscosity sensor. For example, when a flow channel is at least partially blocked, the pressures measured by the viscosity sensor (e.g., two or more pressures sensors of the viscometer) are higher than the pressure of the gas at the source.

In some embodiments, performing the measurement with the viscosity sensor includes converting the pressures of the gas to a flow rate of the gas. For example, when a flow channel is at least partially blocked, the flow rate is less than a predetermined flow rate (e.g., the flow rate of a healthy viscometer).

In some embodiments, the method includes (842) calibrating the viscometer using a preselected reference liquid independent of a user input. For example, in some embodiments, a viscosity of a preselected reference liquid is measured and the measured viscosity is compared with a viscosity, of the preselected referenced liquid, stored prior to the measurement (also called herein a previously known viscosity of the preselected reference liquid). In some embodiments, subsequent viscosity measurements are adjusted based on a difference between the measured viscosity and the previously known viscosity of the preselected reference liquid. In some embodiments, the viscosity of the preselected reference liquid is measured at multiple temperatures, and measured viscosity values at the multiple temperatures are used to calibrate the viscometer. In some embodiments, multiple preselected reference liquids are used to calibrate the viscometer.

In some embodiments, the method includes (844) measuring one or more of: a pH, a density, and a conductivity of the liquid. In some embodiments, the pH and the conductivity of the liquid are concurrently measured. In some embodiments, the pH and the viscosity of the liquid are concurrently measured. In some embodiments, the conductivity and the viscosity of the liquid are concurrently measured. In some embodiments, the density and the viscosity of the liquid are concurrently measured. In some embodiments, the density and the pH of the liquid are concurrently measured. In some embodiments, the density and the conductivity of the liquid are concurrently measured.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A viscometer, comprising:
a viscosity sensor with a liquid flow channel and at least two pressure sensors positioned along the liquid flow channel and configured to measure a pressure drop of a liquid flowing through the liquid flow channel;
a dispensing mechanism configured to couple with a syringe coupled with the viscosity sensor for providing the liquid to the viscosity sensor; and
an electronic controller configured to control operations of the dispensing mechanism and receive and process data from the viscosity sensor so that the dispensing mechanism, controlled by the electronic controller, causes dispensing of the liquid from the syringe to the viscosity sensor and retrieval of the liquid from the viscosity sensor to the syringe at a known rate so that the pressure drop of the liquid flowing through the liquid flow channel is measured while the liquid is retrieved from the viscosity sensor to the syringe.

2. The viscometer of claim 1, wherein the syringe includes a barrel and a plunger and the dispensing mechanism includes an adaptor coupled to the plunger so that the plunger is pushed by moving the adaptor of the dispensing mechanism and the plunger is pulled by moving the adaptor of the dispensing mechanism.

3. The viscometer of claim 2, further comprising a positive pressure source coupled with an outlet of the viscosity sensor.

4. The viscometer of claim 1, further comprising a selection valve coupled with the viscosity sensor and the syringe and located between the viscosity sensor and the syringe.

5. A viscometer, comprising:
a viscosity sensor with a liquid flow channel and at least two pressure sensors positioned along the liquid flow channel and configured to measure a pressure drop of a liquid flowing through the liquid flow channel;
a dispensing mechanism configured to couple with a syringe coupled with the viscosity sensor for providing the liquid to the viscosity sensor; and
an electronic controller configured to control operations of the dispensing mechanism and receive and process data from the viscosity sensor so that the dispensing mechanism, controlled by the electronic controller, causes dispensing of the liquid from the syringe to the viscosity sensor and retrieval of the liquid from the viscosity sensor to the syringe at a known rate, wherein:
the viscometer is configured to couple with a source of gas and provide the gas through the liquid flow channel; and
the viscometer is configured to determine whether the viscosity sensor is operating within predefined criteria based on one or more measurements for the gas.

6. The viscometer of claim 5, wherein the electronic controller is configured to determine that the viscosity sensor is operating within predefined criteria based on one or more pressures of the gas measured by the pressure sensors of the viscosity sensor.

7. The viscometer of claim 6, wherein the viscosity sensor includes a monolithic sensor plate formed by a pressure sensor membrane and a pressure sensor substrate, providing the at least two pressure sensors.

8. A method, comprising:
dispensing, using the dispensing mechanism of the viscometer of claim 1, a liquid from the syringe to the viscosity sensor coupled with the syringe at a known rate, the viscosity sensor being with a liquid flow channel and at least two pressure sensors positioned along the liquid flow channel;
measuring a pressure drop of the liquid flowing through the liquid flow channel while the liquid is dispensed from the syringe to the viscosity sensor;
retrieving, using the dispensing mechanism, the liquid from the viscosity sensor to the syringe at a known rate; and
measuring a pressure drop of the liquid flowing through the liquid flow channel while the liquid is retrieved from the viscosity sensor to the syringe.

9. The method of claim 8, wherein:
dispensing, using the dispensing mechanism, the liquid from the syringe to the viscosity sensor includes pushing a plunger of the syringe by moving an adaptor of the dispensing mechanism; and
retrieving, using the dispensing mechanism, the liquid from the viscosity sensor to the syringe includes pulling the plunger of the syringe by moving the adaptor of the dispensing mechanism back.

10. The method of claim 9, further comprising:
applying a positive pressure on an outlet of the viscosity sensor to increase a speed of retrieving the liquid from the viscosity sensor and avoid damages to the pressure sensors in the viscosity sensor.

11. The method of claim 8, further comprising:
determining a viscosity of the liquid from the pressure drop.

12. A method, comprising:
dispensing, using a dispensing mechanism, a liquid from a syringe to a viscosity sensor coupled with the syringe at a known rate, the viscosity sensor being with a liquid flow channel and at least two pressure sensors positioned along the liquid flow channel;
measuring a pressure drop of the liquid flowing through the liquid flow channel while the liquid is dispensed from the syringe to the viscosity sensor;
retrieving, using the dispensing mechanism, the liquid from the viscosity sensor to the syringe at a known rate;
measuring a pressure drop of the liquid flowing through the liquid flow channel while the liquid is retrieved from the viscosity sensor to the syringe;
coupling the viscosity sensor with a source of gas;
providing the gas through the liquid flow channel of the viscosity sensor; and
measuring pressures of the gas with the pressure sensors of the viscosity sensor.

13. The method of claim 12, further comprising:
determining that the viscosity sensor is operating within predefined criteria based on one or more pressures of the gas measured by the pressure sensors of the viscosity sensor.

14. The method of claim 13, wherein:
the viscosity sensor includes a monolithic sensor plate formed by a pressure sensor membrane and a pressure sensor substrate, providing the at least two pressure sensors.

\* \* \* \* \*